(12) United States Patent
Pan et al.

(10) Patent No.: US 10,100,083 B2
(45) Date of Patent: *Oct. 16, 2018

(54) LEUKEMIA STEM CELL TARGETING LIGANDS AND METHODS OF USE

(71) Applicant: The Regents of the University of California, Oakland, CA (US)

(72) Inventors: Chong-xian Pan, Davis, CA (US); Hongyong Zhang, Davis, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/142,912

(22) Filed: Apr. 29, 2016

(65) Prior Publication Data

US 2016/0237118 A1  Aug. 18, 2016

Related U.S. Application Data

(62) Division of application No. 14/130,909, filed as application No. PCT/US2012/045934 on Jul. 9, 2012, now Pat. No. 9,334,306.

(60) Provisional application No. 61/506,058, filed on Jul. 9, 2011.

(51) Int. Cl.
| | |
|---|---|
| C07K 7/06 | (2006.01) |
| G01N 33/574 | (2006.01) |
| A61K 51/08 | (2006.01) |
| A61K 47/62 | (2017.01) |
| A61K 47/69 | (2017.01) |

(52) U.S. Cl.
CPC .............. C07K 7/06 (2013.01); A61K 47/62 (2017.08); A61K 47/6907 (2017.08); A61K 51/08 (2013.01); G01N 33/57426 (2013.01); *C07K 2319/30* (2013.01); *G01N 2333/7056* (2013.01)

(58) Field of Classification Search
CPC ...................................................... C07K 7/06
See application file for complete search history.

(56) References Cited

U.S. PATENT DOCUMENTS

| | | | | |
|---|---|---|---|---|
| 6,027,912 A * | 2/2000 | Hall | ...................... | C07K 14/705 435/252.3 |
| 6,551,795 B1 * | 4/2003 | Rubenfield | ............ | C07K 14/21 435/253.3 |
| 6,833,447 B1 * | 12/2004 | Goldman | ................ | C12Q 1/689 435/252.3 |
| 7,001,743 B2 * | 2/2006 | Cosgrove | ............. | C07K 14/415 435/419 |
| 7,015,001 B2 * | 3/2006 | Baltz | .................... | C07K 14/195 435/252.3 |
| 7,101,872 B2 * | 9/2006 | Bachmann | ........... | C07D 243/38 514/220 |
| 7,214,786 B2 * | 5/2007 | Kovalic | ............... | C07K 14/415 530/324 |
| 7,452,965 B2 | 11/2008 | Kelly et al. | | |
| 7,504,490 B1 * | 3/2009 | Weinstock | ............. | C07K 14/38 435/252.3 |
| 8,119,410 B2 * | 2/2012 | Reed | .................. | C07K 14/4747 435/7.92 |
| 8,232,533 B2 * | 7/2012 | Kingsley | .............. | C09K 11/025 250/459.1 |
| 8,809,059 B2 * | 8/2014 | Biasing | .............. | C12N 15/8261 435/419 |
| 9,334,306 B2 * | 5/2016 | Pan | ................... | C01N 33/57426 |
| 2003/0233675 A1 * | 12/2003 | Cao | ...................... | C07K 14/195 800/279 |
| 2004/0210036 A1 * | 10/2004 | Dwyer | .................. | C07K 1/047 530/350 |
| 2004/0254120 A1 * | 12/2004 | Fogelman | ............ | A61K 31/366 514/1.1 |
| 2007/0061916 A1 * | 3/2007 | Kovalic | ............... | C07K 14/415 800/278 |
| 2009/0100536 A1 * | 4/2009 | Adams | ................... | A01N 25/34 800/260 |
| 2009/0253896 A1 * | 10/2009 | Smith | ................ | A61K 49/0021 530/328 |
| 2012/0230994 A1 | 9/2012 | Pan et al. | | |
| 2014/0248633 A1 | 9/2014 | Pan et al. | | |

FOREIGN PATENT DOCUMENTS

| | | |
|---|---|---|
| CN | 103764668 | 4/2014 |
| CN | 201280040039.5 | 8/2016 |
| EP | 2729486 | 12/2017 |
| WO | 2001/042277 | 6/2001 |
| WO | 2003/086284 | 10/2003 |
| WO | 2004/108948 | 12/2004 |
| WO | 2006/054262 | 5/2006 |
| WO | 2007/092627 | 8/2007 |
| WO | 2007/104062 | 9/2007 |
| WO | 2009/090651 | 7/2009 |
| WO | 2011/038142 | 3/2011 |
| WO | 2013/009690 | 1/2013 |

OTHER PUBLICATIONS

U.S. Appl. No. 14/130,909, Office Action dated Apr. 6, 2015.
U.S. Appl. No. 14/130,909, Notice of Allowance dated Jan. 21, 2016.
CN patent application No. 201280040039.5, Office Action dated May 5, 2015.
CN patent application No. 201280040039.5, Office Action dated Dec. 1, 2015.
CN patent application No. 201280040039.5, Notice to Grant Patent dated May 4, 2016.

(Continued)

*Primary Examiner* — Amber D Steele
(74) *Attorney, Agent, or Firm* — Mintz, Levin, Cohn, Ferris, Glovsky and Popeo, P.C.

(57) ABSTRACT

The present invention is directed to C-type lectin-like molecule-1 (CLL1) specific ligand peptides, comprising the amino acid motif LR(S/T), and methods of their use, e.g., for imaging detection for diagnosis of leukemia and the presence of leukemic stem cells (LSCs) and targeted therapy against leukemia mediated at least in part by CLL1-expressing LSCs.

32 Claims, 16 Drawing Sheets

Specification includes a Sequence Listing.

(56) References Cited

OTHER PUBLICATIONS

EP patent application No. 12811317.2, European Search Report dated Mar. 4, 2015.
EP patent application No. 12811317.2, Office Action dated Nov. 5, 2015.
WO patent application No. PCT/US2012/045934, International Search Report and Written Opinion dated Dec. 6, 2012.
WO patent application No. PCT/US2012/045934, International Preliminary Report on Patentability dated Jan. 14, 2014.
Bakker et al., (2004) "C-Type Lectin-Like Molecule-1: A novel myeloid cell surface marker associated with acute myeloid leukemia," *Cancer Research*, 64: 8443-8450.
Luo et al., (2008) "Rainbow Beads: a color coding method to facilitate high-throughput screening and optimization of one-bead one-compound combinatorial libraries," *J. Comb. Chem.* 10: 599-604.
Xiao et al., (Oct. 1, 2010) "A self-assembling nanoparticle for paclitaxel delivery in ovarian cancer," *NIH-PA Author Manuscript*; available in PMC Oct. 1, 2010, 24 pages; Published in final edited form as *Biomaterials*, Oct. 2009; 30(30): 6006-6016. Doi:10.1016/j.biomaterials.2009.07.015.
Zhang et al., (2014) "Nanomicelle formulation modifies the pharmacokinetic profiles and cardiac toxicity of daunorubicin," *Nanomedicine*, ISSN 1743-5889 14 pages.
EP patent application No. 12811317.2, Office Action dated Dec. 1, 2016.

\* cited by examiner

LEUKEMIA STEM CELL TARGETING LIGANDS AND METHODS OF USE

CROSS-REFERENCE TO RELATED APPLICATIONS

This application is a divisional of U.S. application Ser. No. 14/130,909, filed on May 15, 2014, issued as U.S. Pat. No. 9,334,306 on May 10, 2016, which is a U.S. national phase under 35 U.S.C. § 371 of International Appl. No. PCT/US2012/045934, filed on Jul. 9, 2012, which claims the benefit under 35 U.S.C. § 119(e) of U.S. Provisional Application No. 61/506,058, filed on Jul. 9, 2011, which are hereby incorporated herein by reference in their entirety for all purposes.

SEQUENCE LISTING

The instant application contains a Sequence Listing which has been submitted electronically in ASCII format and is hereby incorporated by reference in its entirety. Said ASCII copy, created on Jan. 24, 2014, is named UCDVP064US-2011-518-2$_{13}$ SL. txt and is 10,951 bytes in size.

FIELD OF THE INVENTION

The present invention relates to peptides and polypeptides comprising an LR(S/T) amino acid motif, alone and conjugated to an effector moiety, and uses of such peptides/polypeptides and conjugates thereof in the treatment and prevention of leukemia, particularly acute myeloid leukemia or acute myelogenous leukemia (AML).

BACKGROUND OF THE INVENTION

The concept of cancer stem cells has tremendous implications for the management of cancer [Pan, et al., *Future Oncol* (2006) 2:723-731; and Misaghian, et al., *Leukemia* (2009) 23:25-42]. Cancer stem cells have been identified in both hematological and solid malignancies, suggesting that the existence of cancer stem cells is a common feature of most malignancies. These cells can self-renew and regenerate more cancer cells. In order to effectively treat and prevent cancer, cancer stem cells must be reduced or eliminated. However, cancer stem cells exhibit a higher level of chemoresistance compared to their progeny cancer cells [Terpstra, et al., *Blood* (1996) 88:1944-1950; and Copland, et al., *Blood* (2006) 107:4532-4539]. The present invention is based, in part, on the demonstration of the feasibility of using drug-loaded nanoparticles that are engineered to bind with high affinity and specificity to acute myeloid leukemia (AML) stem cells (LSC).

Under present protocols, chemoresistance of LSC can be overcome with high-dose chemotherapy followed by bone marrow transplantation. However, high-dose chemotherapy is associated with severe toxicity and high therapy-related mortality. Many patients are not eligible for this treatment because of co-morbidities. This is especially true for AML patients with a median age at diagnosis of 60 to 65 years and usually associated with multiple co-morbidities. For bone marrow transplantation, autologous bone marrow or stem cells are usually not used because of contamination by LSC. Allogeneic hematopoietic stem cell transplantation is often associated with severe graft-versus-host disease, and is commonly not offered to elderly patients.

Among cancer stem cell types, AML LSC have been best characterized. Many of the cell surface molecules on LSC are known. For example, the C-type lectin-like molecule-1 (CLL1) is known to be preferentially expressed on most AML LSC. Even though CLL1 is also expressed on CD38 (+) myeloid progenitor cells, it is not on CD34(+)/CD38(−) hematopoietic stem cells [Bakker, et al., *Cancer Res* (2004) 64:8443-8450; and van Rhenen et al., *Blood* (2007) 110: 2659-2666]. It has been shown that CLL1 can be potentially targeted for the treatment of AML [Zhao, et al., *Haematologica* (2010) 95:71-78].

Recently, a biocompatible nanomicelle drug delivery system comprised of a unique amphiphilic polymers called telodendrimers was developed [Xiao, et al., *Biomaterials* (2009) 30:6006-6016; Luo, et al., *Bioconjug Chem* (2010) 21:1216-1224]. Telodendrimers consist of cholic acid, lysine and polyethylene glycol (PEG) covalently conjugated together, which impart the ability to self-assemble into a water-soluble spheroid with a hydrophobic core capable of sequestering many types of drugs. Cholic acid, a primary component of bile acid, possesses a facial amphiphilic structure: a rigid steroid scaffold with four hydrophilic groups on one surface, and hydrophobic methyl groups on the other surface of the scaffold. Lysine is a natural amino acid. PEG is biocompatible and has been used to improve the pharmacokinetics of therapeutic drugs. This nanocarrier system has many attractive characteristics for drug delivery, such as high drug loading capacity, narrow polydispersity, well-defined structure, easy chemical modification, superior physical, chemical stability and biocompatibility.

The present invention is based, in part on the discovery of a series of peptides via the phage-display library method that bind specifically to CLL1. One of these ligands, CLL1-L1, was used to decorate the surface of nanomicelles to form a targeting nanoplatform that we named "LSC-targeting nanomicelles." Unlike solid tumors that primarily reside at the extravascular space and are accessible by nanotherapeutics mainly through enhanced permeability and retention effect, LSC and leukemic cells reside primarily inside blood vessels and bone marrow that are directly accessible by nanotherapeutics through intravenous administration. Data provided herein demonstrate that targeting nanomicelles displaying CLL1-L1 bind to the surface of cells expressing CLL1, and deliver the nanomicelles and their effector cargo into the target cells.

SUMMARY OF THE INVENTION

The present invention provides peptides that preferentially or specifically bind to C-type lectin-like molecule-1 (CLL1), the peptides comprising the amino acid motif LR(S/T). The peptides find use in reducing, inhibiting and/or preventing the proliferation or growth of leukemia stem cells expressing (CLL1).

Accordingly, in one aspect, the invention provides peptides comprising the amino acid sequence motif LR(S/T), wherein the peptide is no longer than 10 amino acids in length and binds to C-type lectin-like molecule-1 (CLL1). In some embodiments, the peptide is no longer than 9 amino acids in length. In some embodiments, the peptide is no longer than 8 amino acids in length. In some embodiments, the peptide is no longer than 7 amino acids in length.

With respect to embodiments of the peptides, in some embodiments, the peptides comprise the amino acid sequence $X_1LRX_4X_5X_6X_7$ (SEQ. ID. NO: 1), wherein:
  $X_1$ is any amino acid;
  $X_4$ is S or T;
  $X_5$ is A, S or F;
  $X_6$ is A, G or S; and
  $X_7$ is A, V, P or F.

In some embodiments, the peptides comprise the amino acid sequence $X_1LRX_4X_5X_6X_7$ (SEQ ID NO: 2), wherein:
  $X_1$ is any amino acid;
  $X_4$ is S or T;
  $X_5$ is A or S;
  $X_6$ is A or G; and
  $X_7$ is A, V or P.

In some embodiments, the peptides comprise the amino acid sequence $X_1LRX_4AAV$ (SEQ ID NO: 3), wherein:
  $X_1$ is any amino acid; and
  $X_4$ is S or T.

In some embodiments, the peptides comprise the amino acid sequence $X_1LRX_4AAX_7$ (SEQ ID NO: 4), wherein:
  $X_1$ is any amino acid;
  $X_4$ is S or T; and
  $X_7$ is A or V. In some embodiments, $X_1$ is P, D, L, T or A.

In some embodiments, the peptides comprise the amino acid sequence $X_1LRSSGP$ (SEQ ID NO: 5), wherein $X_1$ is any amino acid. In some embodiments, $X_1$ is V, S, P or T.

In some embodiments, $X_1$ is any amino acid other than a cysteine residue.

In some embodiments, the peptide is selected from the group consisting of PLRSAAA (SEQ ID NO: 6), DLRSAAV (SEQ ID NO: 7), LLRTAAV (SEQ ID NO: 8), LLRSAAV (SEQ ID NO: 9), TLRTAAV (SEQ ID NO: 10), ALRSAAV (SEQ ID NO: 11), VLRSSGP (SEQ ID NO: 12), SLRSSGP (SEQ ID NO: 13), PLRSSGP (SEQ ID NO: 14), TLRSSGP (SEQ ID NO: 15), and PTPPFSF (SEQ ID NO: 16). In some embodiments, the peptide is DLRSAAV (SEQ ID NO: 7). In some embodiments, the peptide is CDLRSAAVC (SEQ ID NO: 17).

The peptides may be substituted (e.g., at one or two amino acid positions) or modified. For example, in some embodiments, the invention provides a polypeptide or peptide comprising an amino acid sequence as described above and herein, wherein:
  i) one or more of the amino acid residues are D-amino acids;
  ii) the polypeptide or peptide comprises protecting groups at one or both of the N-terminus or the C-terminus;
  iii) the polypeptide or peptide is fully or partially retro-inverso;
  iv) the polypeptide or peptide comprises 2 or more repeats, for example, 3, 4, 5, 6 or more repeats;
  v) the polypeptide or peptide is circularized;
  vi) one or more of the amino acid residues are attached to a peptoid backbone;
  vii) one or more of the amino acid residues are β amino acid residues; or
  viii) the polypeptide or peptide is stabilized with a hydrocarbon staple.

In some embodiments, the peptides bind to C-type lectin-like molecule-1 (CLL1) expressed on the surface of leukemia stem cells (LSCs). Preferably, the peptides do not bind or do not bind significantly to normal blood cells or normal hematopoietic stem cells.

In some embodiments, the peptides further comprise from 1 to 5 flanking amino acid residues at the amino and/or carboxyl termini. In some embodiments, the peptides further comprise a cysteine residue at the amino terminus and a cysteine residue at the carboxyl terminus.

In some embodiments, the CLL1-specific peptide (or repeats thereof) can be embedded within or located within a longer polypeptide sequence, for example, a fusion sequence or another non-naturally occurring polypeptide sequence. In some embodiments, the peptide is linked (e.g., via chemical linkage or fusion) to one or more additional polypeptides, e.g., at the amino and/or carboxyl ends.

In a related embodiment, the invention provides a fusion protein comprising peptide comprising an amino acid sequence as described above and herein, and a second polypeptide (that is heterologous to the peptide). In some embodiments, the second polypeptide is the Fc portion of an immunoglobulin, for example, an IgG. In some embodiments, the second polypeptide is the Fc region of a human IgG1, IgG2, IgG3 or IgG4 isotype. In some embodiments, the second polypeptide is a cytotoxin.

In some embodiments, the peptide is linked to a therapeutic moiety or a detectable label. For example, in some embodiments, the detectable label is an imaging label, a bead, a dye, a fluorophore, a chemiluminscent moiety, a quantum dot, a nanoparticle, a magnetic particle (e.g., an iron oxide particle), a metal particle (e.g., a gold particle), or a radioisotope (e.g., $^3H$, $^{32}P$, $^{125}I$, $^{123}I$, $^{11}C$, $^{13}N$, $^{15}O$, $^{18}F$, $^{82}Rb$, technetium-99m (Tc-99m), thallium-201). In some embodiments, the therapeutic moiety is an Fc portion of an immunoglobulin, a cytotoxin, a nanoparticle, a liposome or a chemotherapeutic agent. In various embodiments, the nanoparticle may be a nanomicelle. In some embodiments, the anticancer agent or chemotherapeutic agent is encapsulated in a liposome or a nanoparticle. In some embodiments, the therapeutic moiety is a chemotherapeutic agent or an anti-neoplastic agent encapsulated in a nanoparticle or a nanocarrier.

In another aspect, the invention provides a nanoparticle or nanocarrier linked to one or more CLL1-specific peptides, as described herein. In various embodiments, the CLL1-specific peptides are covalently bound to the nanoparticle or nanocarrier. The nanoparticle or nanocarrier may further encapsulate or be linked to an effector moiety (e.g., a therapeutic moiety or a detectable label). In some embodiments, the nanoparticle or nanocarrier encapsulate a chemotherapeutic agent or an anti-neoplastic agent. In various embodiments, the nanoparticle or nanocarrier comprise nanoparticles formed by the self-assembly of amphiphilic telodendrimers, e.g., polyethylene glycol-block-dendritic oligo cholic acids.

In a related aspect, the invention provides compositions comprising a CLL1-specific polypeptide or peptide ligand, as described herein, and a pharmaceutically acceptable carrier. In some embodiments, the CLL1-specific peptides are formulated as a nanoparticle.

In a related aspect, the invention provides methods of detecting the presence of a leukemia stem cell (LSC) expressing C-type lectin-like molecule-1 (CLL1). In some embodiments, the methods comprise contacting the LSC with a peptide as described above and herein linked to a detectable label, and detecting the binding of the peptide to the LSC. In various embodiments, the detectable label can be a bead, a fluorophore, a chemiluminescent moiety, a quantum dot, a nanoparticle, a magnetic particle, a metal particle or a radioisotope. In some embodiments, the LSC is in vitro. In some embodiments, the LSC is in vivo. In some embodiments, the LSC are in a population of blood cells.

In some embodiments, the signal for binding of the CLL1-specific peptide is detectable, indicating the presence of leukemia and/or leukemia stem cells. In some embodiments, the signal for binding of the CLL1-specific peptide is not detectable, indicating the absence of leukemia and/or leukemia stem cells. In some embodiments, the signal for binding of the CLL1-specific peptide is above a threshold level, indicating the presence of leukemia and/or leukemia stem cells. In some embodiments, the signal for binding of the CLL1-specific peptide is below a threshold level, indicating the absence of leukemia and/or leukemia stem cells. In some embodiments, the signal for binding of the CLL1-specific peptide is greater than the signal for binding of the CLL1-specific peptide to a normal control tissue (e.g., blood from a subject known to not have leukemia), indicating the presence of leukemia and/or leukemia stem cells. In some embodiments, the signal for binding of the CLL1-specific peptide is about equivalent to or less than the signal for binding of the CLL1-specific peptide to a normal control tissue (e.g., blood from a subject known to not have leukemia), indicating the absence of leukemia and/or leukemia stem cells.

In a further aspect, the invention provides methods of inhibiting, reducing or preventing the growth or proliferation of a leukemia stem cell (LSC) expressing C-type lectin-like molecule-1 (CLL1). In some embodiments, the methods comprise contacting the LSC with a peptide as described above and herein linked to a therapeutic moiety, wherein the peptide binds to LSC and the therapeutic moiety inhibits or prevents the growth or proliferation of the LSC. In some embodiments, the LSC is in vitro. In some embodiments, the LSC is in vivo.

In a further aspect, the invention provides methods of inhibiting, reducing or preventing the growth or proliferation of a leukemia stem cell (LSC) expressing C-type lectin-like molecule-1 (CLL1) in a subject in need thereof. In some embodiments, the methods comprise contacting the LSC with a peptide as described above and herein linked to a therapeutic moiety, wherein the peptide binds to LSC and the therapeutic moiety inhibits or prevents the growth or proliferation of the LSC. In some embodiments, the subject is a mammal, for example, human, non-human primate or canine. In some embodiments, the peptide linked to the therapeutic moiety is administered to the subject intravenously or into the bone marrow. In some embodiments, the subject has, is suspected of having or is at risk of developing acute myelogenous leukemia (AML).

In some embodiments, the therapeutic moiety is an Fc portion of an immunoglobulin, a cytotoxin, a nanoparticle, a liposome or a chemotherapeutic agent.

Definitions

The terms "C-type lectin-like molecule-1," "CLL1," "CLEC12A" refers to a member of the C-type lectin/C-type lectin-like domain (CTL/CTLD) superfamily. Members of this family share a common protein fold and have diverse functions, such as cell adhesion, cell-cell signaling, glycoprotein turnover, and roles in inflammation and immune response. Functionally, CLL1 is a negative regulator of granulocyte and monocyte function. Structurally, CCL1 refers to nucleic acids and polypeptide polymorphic variants, alleles, mutants, and interspecies homologs that: (1) have an amino acid sequence that has greater than about 90% amino acid sequence identity, for example, 91%, 92%, 93%, 94%, 95%, 96%, 97%, 98% or 99% or greater amino acid sequence identity, preferably over a region of at least about 25, 50, 100, 200, 400, or more amino acids, or over the full-length, to an amino acid sequence encoded by a CCL1 nucleic acid (see, e.g., GenBank Accession Nos. NM_138337.5→NP_612210.4 (isoform 1); NM_201623.3→NP_963917.2 (isoform 2); NM_001207010.1→NP_001193939.1 (isoform 3); (2) bind to antibodies, e.g., polyclonal antibodies, raised against an immunogen comprising an amino acid sequence of a CLL1 polypeptide (e.g., CLL1 polypeptides described herein); or an amino acid sequence encoded by a CLL1 nucleic acid (e.g., CLL1 polynucleotides described herein), and conservatively modified variants thereof (3) specifically hybridize under stringent hybridization conditions to an anti-sense strand corresponding to a nucleic acid sequence encoding a CLL1 protein, and conservatively modified variants thereof (4) have a nucleic acid sequence that has greater than about 90%, preferably greater than about 91%, 92%, 93%, 94%, 95%, 96%, 97%, 98%, 99%, or higher nucleotide sequence identity, preferably over a region of at least about 25, 50, 100, 200, 500, 1000, 2000 or more nucleotides, or over the full-length, to a CLL1 nucleic acid (e.g., CLL1 polynucleotides, as described herein, and CLL1 polynucleotides that encode CLL1 polypeptides, as described herein). Based on the knowledge of CLL1 homologs, those of skill can readily determine residue positions that are more tolerant to substitution. For example, amino acid residues conserved amongst species are less tolerant of substitution or deletion. Similarly, amino acid residues that are not conserved amongst species are more tolerant of substitution or deletion, while retaining the function of the CLL1 protein.

A "toxic moiety" is the portion of a chimeric molecule which renders the chimeric molecule cytotoxic to cells of interest.

The term "effector moiety" or "therapeutic moiety" refers to the portion of a chimeric molecule intended to have an effect on a cell targeted by the targeting moiety (e.g., CLL1 peptide ligands described herein) or to identify the presence of the immunoconjugate.

The term "chimeric molecule" includes reference to a covalent linkage of an effector molecule to a CLL1-binding peptide of the invention.

The term "cytotoxin" typically includes reference to abrin, ricin, *Pseudomonas* exotoxin (PE), diphtheria toxin (DT), botulinum toxin, or modified toxins thereof. For example, PE and DT are highly toxic compounds that typically bring about death through liver toxicity. PE and DT, however, can be modified into a form for use as an immunotoxin by removing the native targeting component of the toxin (e.g., domain Ia of PE or the B chain of DT) and replacing it with a different targeting moiety, such as a peptide described herein.

The term "contacting" includes reference to placement in direct physical association.

As used herein, "polypeptide", "peptide" and "protein" are used interchangeably and include reference to a polymer of amino acid residues. As used herein, the term "peptide" is used in its broadest sense to refer to conventional peptides (i.e. short polypeptides containing L or D-amino acids), as well as peptide equivalents, peptide analogs and peptidomimetics that retain the desired functional activity. Peptide equivalents can differ from conventional peptides by the replacement of one or more amino acids with related organic acids (such as PABA), amino acids or the like, or the substitution or modification of side chains or functional groups. The terms apply to amino acid polymers in which one or more amino acid residue is an artificial chemical analogue of a corresponding naturally occurring amino acid, as well as to naturally occurring amino acid polymers. The terms also apply to polymers containing conservative amino acid substitutions such that the protein remains functional.

The terms "peptide equivalents", "peptide analogs", "peptide mimetics", and "peptidomimetics" are used interchangeably unless specified otherwise. Peptide analogs are commonly used in the pharmaceutical industry as non-peptide drugs with properties analogous to those of the template peptides. (Fauchere, J. (1986) Adv. Drug Res. 15: 29; Veber and Freidinger (1985) TINS p. 392; and Evans et al. (1987) J. Med. Chem 30: 1229). Peptide analogs are usually developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (e.g., a polypeptide that has a biological or pharmacological activity), such as naturally-occurring receptor-binding polypeptide, but have one or more peptide linkages optionally replaced by a linkage selected from the group consisting of: —CH$_2$NH—, —CH$_2$S—, —CH$_2$—CH$_2$—, —CH═CH— (cis and trans), —COCH$_2$—, —CH(OH) CH$_2$—, and —CH$_2$SO—, by methods known in the art and further described in the following references: Spatola, A. F. in "Chemistry and Biochemistry of Amino Acids, Peptides, and Proteins," B. Weinstein, eds., Marcel Dekker, New York, p. 267 (1983); Spatola, A. F., Vega Data (March 1983), Vol. 1, Issue 3, "Peptide Backbone Modifications" (general review); Morley, J. S., Trends Pharm Sci (1980) pp. 463-468 (general review); Hudson, D. et al., Int J Pept Prot Res (1979) 14:177-185 (—CH$_2$NH—, CH$_2$CH$_2$—); Spatola, A. F. et al., Life Sci (1986) 38:1243-1249 (—CH$_2$S); Hann, M. M., J Chem Soc Perkin Trans I (1982) 307-314 (—CH═CH—, cis and trans); Almquist, R. G. et al., J Med Chem (1980) 23:1392-1398 (—COCH$_2$—); Jennings-White, C. et al., Tetrahedron Lett (1982) 23:2533 (—COCH$_2$—); Szelke, M. et al., European Appln. EP 45665 (1982) CA: 97:39405 (1982) (—CH(OH)CH$_2$—); Holladay, M. W. et al., Tetrahedron Lett (1983) 24:4401-4404 (—C(OH)CH$_2$—); and Hruby, V. J., Life Sci (1982) 31:189-199 (—CH$_2$—S—). Portions or all of the peptide backbone can also be replaced by conformationally constrained cyclic alkyl or aryl substituents to restrict mobility of the functional amino acid sidechains specified herein as described in the following references: 1. Bondinell et al. Design of a potent and orally active nonpeptide platelet fibrinogen receptor (GPIIb/IIIa) antagonist. Bioorg Med Chem 2:897 (1994). 2. Keenan et al. Discovery of potent nonpeptide vitronectin receptor (alpha v beta 3) antagonists. J Med Chem 40:2289 (1997). 3. Samanen et al. Potent, selective, orally active 3-oxo-1,4-benzodiazepine GPIIb/IIIa integrin antagonists. J Med Chem 39:4867 (1996).

The peptides of this invention may be produced by recognized methods, such as recombinant and synthetic methods that are well known in the art. Recombinant techniques are generally described in Sambrook, et al., Molecular Cloning: A Laboratory Manual, (3rd ed.) Vols. 1-3, Cold Spring Harbor Laboratory, (2001). Techniques for the synthesis of peptides are well known and include those described in Merrifield, J. Amer. Chem. Soc. 85:2149-2456 (1963), Atherton, et al., Solid Phase Peptide Synthesis: A Practical Approach, IRL Press (1989), and Merrifield, Science 232:341-347 (1986). See also, Lam, et al., Nature (1991) 354:82-84; Lam, et al., Chem Rev (1997) 97:411-448; and Zhang, et al., Urol Oncol (2011) PMID:20888272.

The term "residue" or "amino acid residue" or "amino acid" includes reference to an amino acid that is incorporated into a protein, polypeptide, or peptide (collectively "peptide"). The amino acid can be a naturally occurring amino acid and, unless otherwise limited, can encompass known analogs of natural amino acids that can function in a similar manner as naturally occurring amino acids.

The amino acids and analogs referred to herein are described by shorthand designations as follows in Table A:

TABLE A

Amino Acid Nomenclature

| Name | 3-letter | 1-letter |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine | Met | M |
| Methionine sulfoxide | Met (O) | — |
| Methionine methylsulfonium | Met (S—Me) | — |
| Norleucine | Nle | — |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

A "conservative substitution", when describing a protein refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. The following six groups in Table B each contain amino acids that are conservative substitutions for one another:

TABLE B

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton, Proteins: Structures and Molecular Properties, W.H. Freeman and Company, New York (2nd Ed., 1992).

The terms "substantially similar" in the context of a peptide indicates that a peptide comprises a sequence with at least 95%, 96%, 97%, 98%, 99% sequence identity to the reference sequence over a comparison window of 7-10 amino acids. Percentage of sequence identity is determined by comparing two optimally aligned sequences over a comparison window, wherein the portion of the polynucleotide sequence in the comparison window may comprise additions or deletions (e.g., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

As used herein, the term "retro-inverso peptide" refers to a peptide that typically comprises the same amino acid sequence as a peptide having L-amino acids, but whose sequence is comprised partially or entirely of D-amino acids, thus having a reversed stereochemistry from a peptide which is synthesized using L-amino acids. By constructing a peptide using the D-amino acids in inverse order (i.e. the sequences are denoted from left to right, from C-terminal to N-terminal amino acid as opposed to from N-terminal to C-terminal as written or denoted in the case of L-amino acids; see infra), one obtains a retro-inverso peptide that restores the same stereochemistry for the side chains as the parent L-amino acid peptide. Use of retro-inverso peptide sequences minimizes enzymatic degradation and, therefore, extends biological half-life of the peptide moiety. Also, these sequences may favorably alter potential immunogenic properties of the analogous conjugates prepared from normal L-amino acid sequences. The retro-inverso sequences (as free peptides or conjugates) are particularly useful in those applications that require or prefer orally active agents (due to resistance to enzymolysis). For the purposes of the present invention, retro-inverso peptides are denoted by "ri", and are written, from left to right, from the C-terminal to the N-terminal amino acid, e.g. the opposite of typical L-peptide notation. In one embodiment, the retro-inverso peptide of the present invention incorporates all D isomer amino acids. When the retro-inverso peptide incorporate all D isomer amino acids, it is termed a "D-reverse peptide".

The terms "substantially pure," or "isolated" when used to describe peptides, refers to a peptide separated from proteins or other contaminants with which they are naturally associated or with which they are associated during synthesis. In one embodiment, a peptide or polypeptide makes up at least 50% of the total polypeptide content of the composition containing the peptide, and in one embodiment, at least 60%, in one embodiment, at least 75%, in one embodiment at least 90%, and in one embodiment, at least 95% of the total polypeptide content.

The terms "conjugating," "joining," "bonding" or "linking" refer to making two polypeptides into one contiguous polypeptide molecule. In the context of the present invention, the terms include reference to joining a targeting peptide moiety to an effector molecule or effector moiety (EM). The linkage can be either by chemical or recombinant means. Chemical means refers to a reaction between the targeting peptide moiety and the effector molecule such that there is a covalent bond formed between the two molecules to form one molecule.

The term "in vivo" includes reference to inside the body of the organism from which the cell was obtained. "Ex vivo" and "in vitro" means outside the body of the organism from which the cell was obtained.

The phrase "malignant cell" or "malignancy" refers to tumors or tumor cells that are invasive and/or able to undergo metastasis, e.g., a cancerous cell.

As used herein, "mammalian cells" includes reference to cells derived from mammals including humans, rats, mice, guinea pigs, chimpanzees, or macaques. The cells may be cultured in vivo or in vitro.

The term "selectively reactive" refers, with respect to an antigen, the preferential association of a ligand (here, a CLL1-specific peptide ligand), in whole or part, with a cell or tissue bearing that antigen and not to cells or tissues lacking that antigen. It is, of course, recognized that a certain degree of non-specific interaction may occur between a molecule and a non-target cell or tissue. Nevertheless, selective reactivity, may be distinguished as mediated through specific recognition of the antigen. Although selectively reactive ligands bind antigen, they may do so with low affinity. On the other hand, specific binding results in a much stronger association between the ligand and cells bearing the antigen than between the bound ligand and cells lacking the antigen. Specific binding typically results in greater than 2-fold, preferably greater than 5-fold, more preferably greater than 10-fold and most preferably greater than 100-fold increase in amount of bound ligand (per unit time) to a cell or tissue bearing the target antigen as compared to a cell or tissue lacking the target antigen. Specific binding to a protein under such conditions requires a ligand that is selected for its specificity for a particular protein. A variety of assay formats are appropriate for selecting ligands specifically immunoreactive with a particular protein. For example, solid-phase assays are routinely used to ligands that specifically bind to antigens. See Harlow & Lane, ANTIBODIES, A LABORATORY MANUAL, Cold Spring Harbor Publications, New York (1988), for a description of assay formats and conditions that can be used to determine specific binding reactivity.

The term "threshold level" refers to a predetermined level of signal (here, of binding of a CLL1-specific peptide to CLL1, e.g., expressed on leukemia stem cells), above which indicates binding and a positive diagnosis of leukemia, and below which indicates non-binding and a negative diagnosis of leukemia. The level of signal can be based on determinations from a population of individuals.

The terms "patient," "subject," "individual" interchangeably refer to a mammal, for example, a human or a non-human primate, a domesticated mammal (e.g., a canine or feline), an agricultural mammal (e.g., a bovine, porcine, ovine, equine), a laboratory mammal (a mouse, rat, hamster, rabbit).

As used herein, "administering" refers to local and systemic administration, e.g., including enteral, parenteral, pulmonary, and topical/transdermal administration. Routes of administration for the peptides, and fusions and conjugates thereof, that find use in the methods described herein include, e.g., oral (per os (P.O.)) administration, nasal or inhalation administration, administration as a suppository, topical contact, transdermal delivery (e.g., via a transdermal patch), intrathecal (IT) administration, intravenous ("iv") administration, intraperitoneal ("ip") administration, intramuscular ("im") administration, intralesional administration (e.g., intratumoral), or subcutaneous ("sc") administration, or the implantation of a slow-release device e.g., a mini-osmotic pump, a depot formulation, etc., to a subject. Administration can be by any route including parenteral and transmucosal (e.g., oral, nasal, vaginal, rectal, or transdermal). Parenteral administration includes, e.g., intravenous, intramuscular, intra-arterial, intradermal, subcutaneous, intraperitoneal, intraventricular, ionophoretic and intracranial. Other modes of delivery include, but are not limited to, the use of liposomal formulations, intravenous infusion, transdermal patches, etc.

The terms "systemic administration" and "systemically administered" refer to a method of administering a compound or composition to a mammal so that the compound or composition is delivered to sites in the body, including the targeted site of pharmaceutical action, via the circulatory system. Systemic administration includes, but is not limited to, oral, intranasal, rectal and parenteral (e.g., other than through the alimentary tract, such as intramuscular, intravenous, intra-arterial, transdermal and subcutaneous) administration.

The term "co-administer" refers to the simultaneous presence of two active agents in the blood of an individual. Active agents that are co-administered can be concurrently or sequentially delivered.

The phrase "cause to be administered" refers to the actions taken by a medical professional (e.g., a physician), or a person controlling medical care of a subject, that control and/or permit the administration of the agent(s)/compound(s) at issue to the subject. Causing to be administered can involve diagnosis and/or determination of an appropriate therapeutic or prophylactic regimen, and/or prescribing particular agent(s)/compounds for a subject. Such prescribing can include, for example, drafting a prescription form, annotating a medical record, and the like.

The terms "effective amount" or "amount effective to" or "therapeutically effective amount" includes reference to a dosage of a therapeutic agent sufficient to produce a desired result, such as inhibiting, reducing or preventing leukemia stem cell growth or tumor growth; promoting leukemia stem cell reduction or elimination; or blocking, reducing, inhibiting or preventing leukemia stem cell growth, migration or metastasis. The term "effective amount" as used in relation to pharmaceutical compositions, typically refers to the amount of the active ingredient, e.g. the peptides of the invention, which are required to achieve the desired goal. For example, in therapeutic applications, an effective amount will be the amount required to be administered to a patient to result in treatment of the particular disorder for which treatment is sought (e.g., leukemia). The term "treatment of a disorder" denotes the reduction or elimination of symptoms of a particular disorder. Effective amounts will typically vary depending upon the nature of the disorder, the peptides used, the mode of administration, and the size and health of the patient. In one embodiment, the effective amount of the peptides of the invention ranges from 1 µg to 1 g of peptide for a 70 kg patient, and in one embodiment, from 1 µg to 10 mg. In one embodiment, the concentration of peptide (or peptide analog) administered ranges from 0.1 µM to 10 mM, and in one embodiment, from 5 µM to 1 mM, in one embodiment, from 5 µM to 100 µM, and in one embodiment from 5 µM to 40 µM.

As used herein, the terms "treating" and "treatment" refer to delaying the onset of, retarding or reversing the progress of, or alleviating or preventing either the disease or condition to which the term applies (e.g., leukemia), or one or more symptoms of such disease or condition.

The terms "inhibiting," "reducing," "decreasing" with respect to tumor or cancer growth or progression refers to inhibiting the growth, spread, metastasis of a tumor or cancer in a subject by a measurable amount using any method known in the art. The growth, progression or spread of a tumor or cancer is inhibited, reduced or decreased if the tumor burden is at least about 10%, 20%, 30%, 50%, 80%, or 100% reduced in comparison to the tumor burden prior to the co-administration of a peptide of the present invention, e.g., as part of a chimeric molecule. In some embodiments, the growth, progression or spread of a tumor or cancer is inhibited, reduced or decreased by at least about 1-fold, 2-fold, 3-fold, 4-fold, or more in comparison to the tumor burden prior to administration of the peptide.

DETAILED DESCRIPTION

1. Introduction

Figure 1A:
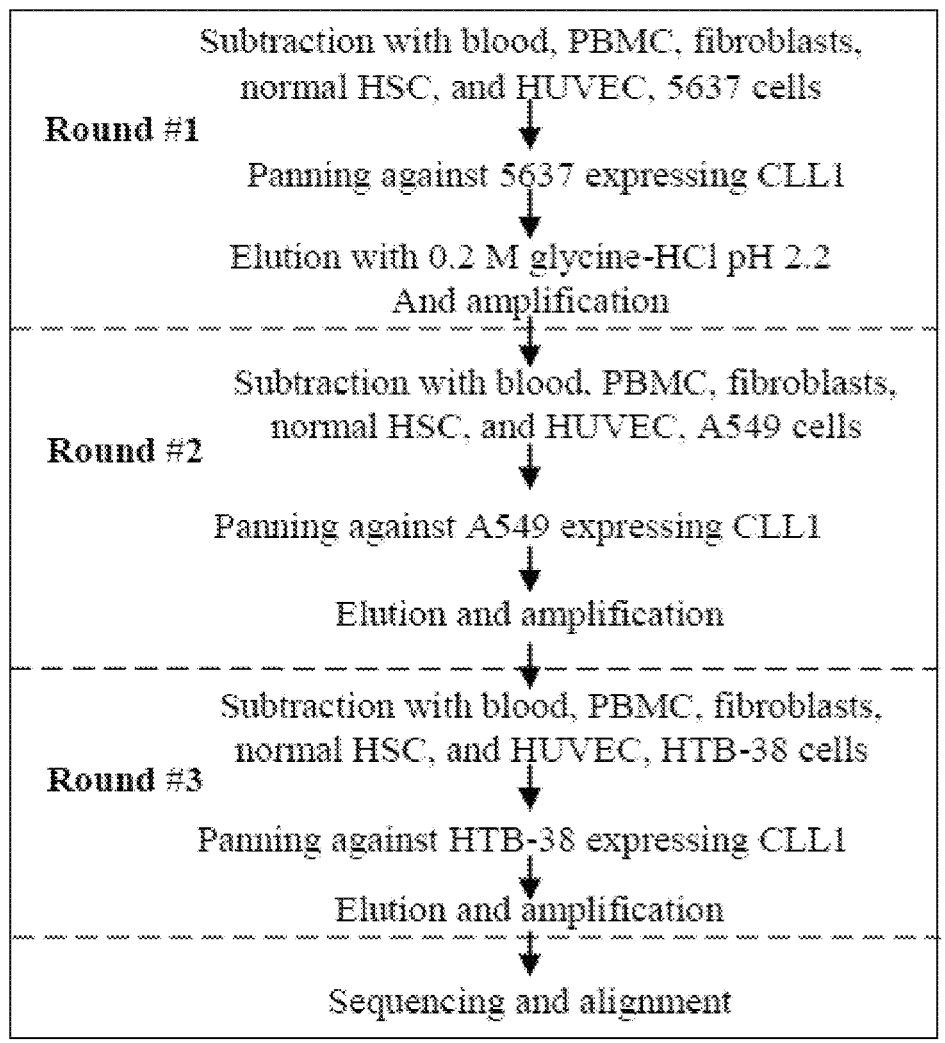
FIGS. 1A-D illustrate identification of peptides that target CLL1. A. Panning strategy to identify CLL1-targeting peptides. Before each round of panning, the C7C phage peptide display library was subtracted with various cells to remove phage that could bind to those confounding cell types. B. Binding of phage to cells expressing CLL1. A549 cells were transfected with CLL1-RFP (a) or RFP (b, control), incubated with phage expressing the CDLRSAAVC (SEQ ID NO: 17)peptide, and probed with anti-M13 phage antibody conjugated with FITC. Binding of phage to A549 cells expressing CLL1-RFP (c), but not to A549 cells expressing RFP (d) was observed. C. Binding of the CDLRSAAVC (SEQ ID NO: 17)peptide to CLL1. Biotinylated CDLRSAAVC (SEQ ID NO: 17) peptide was synthesized and used to probe PBMC, A549 transfected with vector alone, and A549 cells expressing CLL1. Specific binding was observed to A549 cells expressing CLL1, but minimal binding was observed with PBMC or A549 cells transfected with vector alone, or when A549 cells expressing CLL1 but probed with a bladder cancer-specific ligand PLZ4 (the most right panel). Upper panel: cells were probed with streptavidin (SA)-FITC. Lower panels: cells were probed with CLL1-targeting peptide and SA-FITC. D. Binding specificity of the CDLRSAAVC (SEQ ID NO: 17)peptide. Cells of various origins were incubated with the biotinylated CLL1-targeting peptide or a bladder cancer-specific peptide, named PLZ4 as a negative control, and probed with SA-PE.

The present invention is based, in part, on the discovery of peptides and polypeptides comprising an LR(S/T) motif specifically bind to the C-type lectin-like molecule-1 (CLL1), a protein that is preferentially expressed on acute myeloid leukemia stem cells (LSC). Accordingly, such peptides and polypeptides find use in the preferential targeting of acute myeloid leukemia stem cells (LSC) expressing C-type lectin-like molecule-1 (CLL1). In various embodiments, peptides and polypeptides comprising an LR(S/T) motif comprise a targeting moiety that can be conjugated to an effector moiety.

In some embodiments, the effector moiety is a nanoparticle. Micellar nanoparticles formed by the self-assemble of the amphiphilic telodendrimers (polyethylene glycol-block-dendritic oligo cholic acids) can be covalently decorated with CLL1-targeting peptides for targeted drug delivery of an anti-neoplastic agent, e.g., daunorubicin, in AML treatment and prevention. Peptide-coated nanoparticles described herein were approximately 13.5 nm in diameter and could be loaded with up to 5 mg of daunorubicin per 20 mg of telodendrimer. These "targeting nanomicelles" transported the drug load to the interior of cells expressing recombinant CLL1 and to LSC isolated from clinical specimens in vitro, but did not bind to normal blood or normal hematopoietic stem cells. The presence of CLL1-targeting peptides on surface of the nanomicelles enabled the improved binding and delivery of substantially more daunorubicin into the cells expressing CLL1 and CD34+ leukemic cells compared to unmodified nanomicelles. Nanomicelles coated with CLL1-targeting peptides find use for eradicating LSC and improving leukemia therapy.

2. C-Type Lectin-Like Molecule-1 (CLL1) Targeting Moieties

The present invention provides peptide ligands that preferentially and/or specifically bind to C-type lectin-like molecule-1 (CLL1), e.g., expressed on the surface of leukemia stem cells (LSCs) and that bind minimally to or do not bind to normal blood cells or normal hematopoietic stem cells. Generally, the CLL1-specific peptide ligands comprise the amino acid motif LR(S/T) and are about 7 to 10 or 7 to 9 amino acids in length. In some embodiments, the peptide is no longer than 10 amino acids in length, for example, no longer than 9, 8 or 7 amino acids in length.

In various embodiments, the peptides comprise the amino acid sequence $X_1LRX_4X_5X_6X_7$ (SEQ ID NO: 1), wherein:
$X_1$ is any amino acid (e.g., A, D, E, F, G, H, I, K, L, M, N, P, Q, R, S, T, V, W, Y and optionally C);
$X_4$ is S or T;
$X_5$ is A, S or F;
$X_6$ is A, G or S; and
$X_7$ is A, V, P or F.

In some embodiments, the peptides comprise the amino acid sequence $X_1LRX_4X_5X_6X_7$ (SEQ ID NO: 2), wherein:
$X_1$ is any amino acid (e.g., A, D, E, F, G, H, I, K, L, M, N, P, Q, R, S, T, V, W, Y and optionally C);
$X_4$ is S or T;
$X_5$ is A or S;
$X_6$ is A or G; and
$X_7$ is A, V or P.

In some embodiments, the peptides comprise the amino acid sequence $X_1LRX_4AAX_7$ (SEQ ID NO: 4), wherein:
$X_1$ is any amino acid (e.g., A, D, E, F, G, H, I, K, L, M, N, P, Q, R, S, T, V, W, Y and optionally C);
$X_4$ is S or T; and
$X_7$ is A or V. In some embodiments, $X_1$ is P, D, L, T or A.

In some embodiments, the peptides comprise the amino acid sequence $X_1LRX_4AAV$ (SEQ ID NO: 3), wherein:
$X_1$ is any amino acid (e.g., A, D, E, F, G, H, I, K, L, M, N, P, Q, R, S, T, V, W, Y and optionally C); and
$X_4$ is S or T.

In some embodiments, the peptides comprise the amino acid sequence $X_1LRSSGP$ (SEQ ID NO: 5), wherein $X_1$ is any amino acid (e.g., A, D, E, F, G, H, I, K, L, M, N, P, Q, R, S, T, V, W, Y and optionally C).

In some embodiments, $X_1$ is any amino acid other than a cysteine residue.

In some embodiments, the peptide is selected from the group consisting of PLRSAAA (SEQ ID NO: 6), DLRSAAV (SEQ ID NO: 7), LLRTAAV (SEQ ID NO: 8), LLRSAAV (SEQ ID NO: 9), TLRTAAV (SEQ ID NO: 10), ALRSAAV (SEQ ID NO: 11), VLRSSGP (SEQ ID NO: 12), SLRSSGP (SEQ ID NO: 13), PLRSSGP (SEQ ID NO: 14), TLRSSGP (SEQ ID NO: 15), and PTPPFSF (SEQ ID NO: 16). In some embodiments, the peptide is DLRSAAV (SEQ ID NO: 7).

The peptides can further comprise from 1 to 5 flanking amino acid residues at the amino and/or carboxyl termini. In some embodiments, the peptides further comprise a cysteine residue at the amino terminus and a cysteine residue at the carboxyl terminus. In some embodiments, the peptides may have from 1 to 5 flanking L- or D-cysteine residues at the N-terminal and C-terminal ends, e.g., to allow for circularization and/or conjugation of the peptide.

For example, in various embodiments, the peptides comprise the amino acid sequence $CX_1LRX_4X_5X_6X_7C$ (SEQ ID NO: 18), wherein:
$X_1$ is any amino acid other than C (e.g., A, D, E, F, G, H, I, K, L, M, N, P, Q, R, S, T, V, W and Y);
$X_4$ is S or T;

X₅ is A, S or F;
X₆ is A, G or S; and
X₇ is A, V, P or F.

In some embodiments, the peptides comprise the amino acid sequence CX₁LRX₄X₅X₆X₇C (SEQ ID NO: 19), wherein:
X₁ is any amino acid other than C (e.g., A, D, E, F, G, H, I, K, L, M, N, P, Q, R, S, T, V, W and Y);
X₄ is S or T;
X₅ is A or S;
X₆ is A or G; and
X₇ is A, V or P.

In some embodiments, the peptides comprise the amino acid sequence X₁LRX₄AAX₇ (SEQ ID NO: 20), wherein:
X₁ is any amino acid other than C (e.g., A, D, E, F, G, H, I, K, L, M, N, P, Q, R, S, T, V, W and Y);
X₄ is S or T; and
X₇ is A or V. In some embodiments, X₁ is P, D, L, T or A.

In some embodiments, the peptides comprise the amino acid sequence CX₁LRX₄AAVC (SEQ ID NO: 21), wherein:
X₁ is any amino acid other than C (e.g., A, D, E, F, G, H, I, K, L, M, N, P, Q, R, S, T, V, W and Y); and
X₄ is S or T.

In some embodiments, the peptides comprise the amino acid sequence CX₁LRSSGPC (SEQ ID NO: 22), wherein X₁ is any amino acid other than C (e.g., A, D, E, F, G, H, I, K, L, M, N, P, Q, R, S, T, V, W and Y).

In some embodiments, the peptide is selected from the group consisting of CPLRSAAAC (SEQ ID NO: 23), CDLRSAAVC (SEQ ID NO: 17), CLLRTAAVC (SEQ ID NO: 25), CLLRSAAVC (SEQ ID NO: 26), CTLRTAAVC (SEQ ID NO: 27), CALRSAAVC (SEQ ID NO: 28), CVLRSSGPC (SEQ ID NO: 29), CSLRSSGPC (SEQ ID NO: 30), CPLRSSGPC (SEQ ID NO: 31), CTLRSSGPC (SEQ ID NO: 32), and CPTPPFSFC (SEQ ID NO: 33). In some embodiments, the peptide is CDLRSAAVC (SEQ ID NO: 17).

The peptides may be substituted (e.g., at one or two amino acid positions) or modified. For example, in some embodiments, the invention provides a polypeptide or peptide comprising an amino acid sequence as described above and herein, wherein:
i) one or more of the amino acid residues are D-amino acids;
ii) the polypeptide or peptide comprises protecting groups at one or both of the N-terminus or the C-terminus;
iii) the polypeptide or peptide is fully or partially retro-inverso;
iv) the polypeptide or peptide comprises 2 or more repeats, for example, 3, 4, 5, 6 or more repeats; the repeats may be the same or different peptides;
v) the polypeptide or peptide is circularized;
vi) one or more of the amino acid residues are attached to a peptoid backbone;
vii) one or more of the amino acid residues are β amino acid residues; or
viii) the polypeptide or peptide is stabilized with a hydrocarbon staple.

One or more of the amino acids in the CLL1-specific peptides can be D-amino acids. In some embodiments, all amino acid residues in the peptide ligands are D-amino acids. In various embodiments, the peptide ligands are partial retro-inverso or full-retro-inverso.

Generally, the CLL1-specific peptides are substantially purified and/or isolated.

In some embodiments, the CLL1-specific peptide (or repeats thereof) can be embedded within or located within a longer polypeptide sequence, for example, a fusion sequence or another non-naturally occurring polypeptide sequence. In some embodiments, the peptide is linked (e.g., via chemical linkage or fusion) to one or more additional polypeptides, e.g., at the amino and/or carboxyl ends. In various embodiments, the polypeptide is no longer than 300 amino acids in length, for example, no longer than 250, 200, 150, 100, 75, 50 or 25 amino acids in length, and binds to CLL1, e.g., expressed on the surface of leukemia stem cells (LSCs).

3. Effector Moieties

In various embodiments, the peptides are linked or conjugated to an effector moiety. As appropriate or desired, the effector moiety can be a detectable label and/or a therapeutic moiety.

Additional amino acid residues or polypeptide sequences may optionally be linked (e.g., either via chemical linkage or fusion) to either the amino and/or carboxy termini of the peptide ligands. In some embodiments, the CLL1-specific peptide sequences described herein can be embedded within or located within a longer polypeptide sequence, for example, a fusion sequence or another non-naturally occurring polypeptide sequence. For example, in various embodiments, the peptides are linked to the Fc portion of an immunoglobulin (e.g., to promote antibody-dependent cellular cytotoxicity (ADCC) and/or complement-dependent cytotoxicity (CDC)) or to a cytotoxin. In some embodiments, the CLL1-specific peptide ligand is linked to the Fc region of an IgG antibody. In some embodiments, the CLL1-specific peptide ligand is linked to the Fc region of a human IgG1, IgG2, IgG3 or IgG4 isotype.

In some embodiments, the CLL1-specific peptide ligands are conjugated to a therapeutic agent. In some embodiments, the therapeutic agent is an anti-neoplastic agent. Illustrative chemotherapeutic agents that can be encapsulated in the nanocarrier are known in the art and include without limitation alkylating agent(s) (e.g., nitrogen mustards, nitrogen ureas, ethylenimines, methylmelamines, alkyl sulfonates, carmustine, triazenes), platinum-coordination complexes (e.g., cisplatin, carboplatin, and oxaliplatin), antimetabolite(s) (e.g., folic acid analogs (e.g., methotrexate), pyrimidine analogs (e.g., capecitabine, 5-fluorouracil, 5-fluorodeoxyuridine, 5-fluorodeoxyuridine monophosphate, cytosine arabinoside, 5-azacytidine, gemcitabine), purine analogs (e.g., mercaptopurine, thioguanine, azathioprine, pentostatin, erythrohydroxynonyladenine, fludarabine, cladribine)), plant alkaloid(s) and/or terpenoid(s), vinca alkaloid(s) (e.g., vincristine, vinblastine, vinorelbine, and vindesine), podophyllotoxin(s) (e.g., etoposide and teniposide), camptothecin(s) (e.g., irinotecan and topotecan), anthracycline(s), aromatase inhibitor(s), taxane(s) (e.g., paclitaxel, taxol and docetaxel), topoisomerase inhibitor(s) (e.g., (Type I inhibitors: camptothecins, including irinotecan and topotecan; Type II Inhibitors: amsacrine, etoposide, etoposide phosphate, and teniposide), antibiotic(s) (e.g., dactinomycin, daunorubicin, doxorubincin, idarubicin, epirubicin, bleomycins, mitomycin), hormone(s), differentiating agent(s), kinase inhibitor(s) (e.g., Bevacizumab, BMW 2992, Cetuximab, Imatinib, Trastuzumab, Gefitinib, Ranibizumab, Pegaptanib, Sorafenib, Dasatinib, Sunitinib, Erlotinib, Nilotinib, Lapatinib, Panitumumab, Vandetanib, E7080, Pazopanib, Mubritinib and Fostamatinib) and antineoplastic agent(s) (e.g., (dactinomycin, doxorubicin, epirubicin, fludarabine and bleomycin). Chemotherapeutic agents of use are known in the art and described in reference texts, e.g., Physicians' Desk Reference, 65th Ed., 2011, Thomson Healthcare or Brunton, et al., Goodman & Gilman's The Pharmacological Basis of Therapeutics, 12th edition, 2010, McGraw-Hill Professional). Any chemotherapeutic agent being used to treat the cancer of interest can be conjugated to the encapsulated in the nanocarrier conjugated to the bladder cancer-specific peptide ligands. Any chemotherapeutic agent being used to treat the cancer of interest can be conjugated directly to the CLL1-specific peptide ligands. In various embodiments, the chemotherapeutic agent is encapsulated in a liposome or a nanocarrier.

In some embodiments, the therapeutic agent is a cytotoxin. Illustrative cytotoxins that find use include abrin, ricin, *Pseudomonas* exotoxin (PE), diphtheria toxin (DT), botulinum toxin, or modified toxins thereof. Other cytotoxins also find use.

In some embodiments, the CLL1-binding peptides are conjugated to a liposome or a nanoparticle that encapsulates the therapeutic agent. Nanoparticles for encapsulation and delivery of a therapeutic agent are known in the art and can find use. Illustrative nanoparticles include without limitation, e.g., polylactide-co-glycolide nanoparticles for controlled delivery of anticancer agents (Dinarvand, et al., *Int J Nanomedicine*. 2011; 6:877-95); polyethyleneimine (PEI)-As(2)O(3)/Mn(0.5)Zn(0.5)Fe(2)O(4) magnetic nanoliposomes (Wang, et al., *Int J Nanomedicine*. 2011; 6:871-5); redox-responsive poly(ethylene glycol)-b-poly(lactic acid) (MPEG-S S-PLA) nanoparticles (Song, et al., *Colloids Surf B Biointerfaces*. 2011, PMID 21719259); Thiolated Pluronic (Plu-SH) nanoparticles (Abdullah-Al-Nahain, et al., *Macromol Biosci*. 2011, PMID 21717576); and mesoporous silica nanoparticles (MSNs) (Wu, et al., *Chem Commun* (Camb). 2011, PMID 21716992). In one embodiment, the bladder cancer-specific binding peptides are conjugated to biocompatible nanomicelles comprised of cholic acid, lysine and polyethylene glycol (PEG) covalently conjugated together, e.g., described in Xiao, et al., *Biomaterials* (2009) 30:6006-6016; and Luo, et al., *Bioconjug Chem* (2010) 21:1216-1224. Further nanomicelles that find use are described, e.g., in PCT Patent Publ. WO 2010/039496.

In one embodiment, the CLL1-specific binding peptides are conjugated to biocompatible nanomicelles comprised of cholic acid, lysine and polyethylene glycol (PEG) covalently conjugated together, e.g., as described in Xiao, et al., *Biomaterials* (2009) 30:6006-6016; and Luo, et al., *Bioconjug Chem* (2010) 21:1216-1224. Recently, a biocompatible nanomicelle drug delivery system comprised of a unique amphiphilic polymers called telodendrimers was developed [Xiao, et al., *Biomaterials* (2009) 30:6006-6016; Luo, et al., *Bioconjug Chem* (2010) 21:1216-1224]. Telodendrimers consist of cholic acid, lysine and polyethylene glycol (PEG) covalently conjugated together, which impart the ability to self-assemble into a water-soluble spheroid with a hydrophobic core capable of sequestering many types of drugs. Cholic acid, a primary component of bile acid, possesses a facial amphiphilic structure: a rigid steroid scaffold with four hydrophilic groups on one surface, and hydrophobic methyl groups on the other surface of the scaffold. Lysine is a natural amino acid. PEG is biocompatible and has been used to improve the pharmacokinetics of therapeutic drugs. This nanocarrier system has many attractive characteristics for drug delivery, such as high drug loading capacity, narrow polydispersity, well-defined structure, easy chemical modification, superior physical, chemical stability and biocompatibility.

In some embodiments, the peptide is linked to a detectable label. For example, in some embodiments, the detectable label is an imaging label, a bead, a dye, a fluorophore, a chemiluminscent moiety, a quantum dot, a nanoparticle, a magnetic particle (e.g., an iron oxide particle), a metal particle (e.g., a gold particle), or a radioisotope (e.g., $^{3}H$, $^{32}P$, $^{125}I$, $^{123}I$, $^{11}C$, $^{13}N$, $^{15}O$, $^{18}F$, $^{82}Rb$, technetium-99m (Tc-99m), thallium-201). In various embodiments, the CLL1-specific peptide ligands are conjugated to a radioactive isotope, for example, $^{125}I$, $^{32}P$, $^{14}C$, $^{3}H$, $^{35}S$, $^{123}I$, $^{11}C$, $^{13}N$, $^{15}O$, $^{18}F$, $^{82}Rb$ technetium-99m (Tc-99m) or thallium-201. In various embodiments, the CLL1-specific peptide ligands are conjugated to a magnetic particle, for example a magnetic bead or an iron oxide particle (e.g., for magnetic resonance imaging (MRI)). In various embodiments, the targeted nanocarrier or liposome conjugated to the CLL1-specific peptide ligands encapsulate an imaging or contrast agent.

4. Compositions Comprising CLL1-Binding Peptides

The CLL1-specific peptide ligands can be prepared as a variety of pharmaceutical formulations for administration to a patient, including liquid and solid form preparations.

Compositions comprising the CLL1-specific peptide ligands are useful for parenteral, topical, oral, or local administration, including by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, capsules and lozenges. It is recognized that the polypeptides and pharmaceutical compositions of this invention, when administered orally, must be protected from digestion. This is typically accomplished either by complexing the polypeptide with a composition to render it resistant to acidic and enzymatic hydrolysis or by packaging the protein in an appropriately resistant carrier such as a liposome. Means of protecting proteins from digestion are well known in the art.

Compositions comprising the CLL1-specific peptide ligands are particularly useful for parenteral administration, such as intravenous administration or administration into a body cavity or lumen of an organ (e.g., the bone marrow). The compositions for administration will commonly comprise a solution of the polypeptide comprising the polypeptide dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of polypeptide in these formulations can vary widely, and will be selected primarily based on fluid volumes, viscosities, body weight and the like in accordance with the particular mode of administration selected and the patient's needs.

Liquid form pharmaceutical preparations can include solutions, suspensions, and emulsions, for example, water or water/propylene glycol solutions. Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents. For parenteral injection, liquid preparations can be formulated in solution in aqueous polyethylene glycol solution. Transdermal administration can be performed using suitable carriers. If desired, apparatuses designed to facilitate transdermal delivery can be employed. Suitable carriers and apparatuses are well known in the art, as exemplified by U.S. Pat. Nos. 6,635,274, 6,623,457, 6,562,004, and 6,274,166.

In some embodiments, the CLL1-specific peptides are formulated as a nanoparticle. Peptide nanoparticles and methods for their preparation are known in the art and described, e.g., in U.S. Patent Publication No. 2006/0251726, U.S. Patent Publication No. 2004/0126900, U.S. Patent Publication No. 2005/0112089, U.S. Patent Publication No. 2010/0172943, U.S. Patent Publication No. 2010/0055189, U.S. Patent Publication No. 2009/0306335, U.S. Patent Publication No. 2009/0156480, and U.S. Patent Publication No. 2008/0213377, each of which is hereby incorporated herein by reference in its entirety for all purposes. Further nanoparticle formulations that find use are described, e.g., in Emerich and Thanos, *Curr Opin Mol Ther* (2008) 10(2):132-9; Kogan, et al., *Nanomedicine* (2007) 2(3):287-306; Zhang, et al., *Bioconjug Chem* (2008) 19(1): 145-152; Scarberry, et al., *J Am Chem Soc* (2008) 130(31): 10258-10262; and Fraysse-Ailhas, et al., *Eur Cells Materials* (2007) 14(Suppl. 3):115. As appropriate, amino acid sequences may be added to either or both the N-terminus and the C-terminus of the peptide ligands in order to allow assembly and formation of the peptide nanoparticle.

Also contemplated are solid form pharmaceutical formulations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical formulation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The term "unit dosage form", as used in the specification, refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention.

In one embodiment, a pharmaceutical formulation is administered to a patient at a therapeutically effective dose to prevent, treat, or control a disease or malignant condition, such as cancer, e.g., leukemia, particularly targeting leukemic stem cells. The pharmaceutical composition or medicament is administered to a patient in an amount sufficient to elicit an effective therapeutic or diagnostic response in the patient. An effective therapeutic or diagnostic response is a response that at least partially arrests or slows the symptoms or complications of the disease or malignant condition. An amount adequate to accomplish this is defined as "therapeutically effective dose."

5. Methods of Treatment and/or Prevention
   a. Subjects Amenable to Treatment and/or Prevention The CLL1-specific peptide ligands described herein find use in the treatment and prevention of leukemia, particularly a leukemia mediated at least in part by leukemic stem cells expressing CLL1. In some embodiments, the subject has, is suspected of having, or is at risk of developing acute myeloid leukemia (AML), particularly AML mediated at least in part by leukemic stem cells expressing CLL1. In some embodiments, the subject may have or be at risk of developing a subtype of AML, including, e.g., minimally differentiated acute myeloblastic leukemia (M0), acute myeloblastic leukemia, without maturation (M1), acute myeloblastic leukemia, with granulocytic maturation (M2), promyelocytic, or acute promyelocytic leukemia (APL) (M3), acute myelomonocytic leukemia (M4), myelomonocytic together with bone marrow eosinophilia (M4eo), acute monoblastic leukemia (M5a), acute monocytic leukemia (M5b), acute erythroid leukemias, including erythroleukemia (M6a), pure erythroid leukemia (M6b), acute megakaryoblastic leukemia (M7), or acute basophilic leukemia (M8).

The subject may be asymptomatic or exhibiting symptoms of leukemia. The subject may have a familial history of leukemia, e.g., a parent, grandparent or sibling who has been diagnosed with leukemia. The subject may be an adult, a juvenile or a child.

The CLL1-specific peptide ligands can be administered to a patient to effect the inhibition, reduction, retraction or prevention of proliferation or growth of leukemic stem cells (LSCs) that express or overexpress CLL1 on their cell surfaces. In the context of effecting treatment, the patient has leukemia, and administration of the CLL1-specific peptide ligands can reverse, delay or inhibit progression of the disease. In the context of effecting prevention, the patient may be in remission, or may have undergone a bone marrow transplant, and administration of the CLL1-specific peptide ligands can delay, reduce, inhibit or eliminate growth of metastasis or the recurrence of disease.

b. Methods of Administration
      i. Routes of Administration

The CLL1-specific peptide ligands described herein can be formulated into pharmaceutical formulations for administration to a patient. Administration of the pharmaceutical formulations can be by a variety of methods. Methods can include systemic administration, wherein the polypeptide or composition of polypeptides is delivered to sites in the body, including the targeted site of pharmaceutical action, via the circulatory system. Systemic administration includes, but is not limited to, oral and parenteral (e.g., other than through the alimentary tract, such as intramuscular, intravenous, intra-arterial, transdermal and subcutaneous) administration. In other embodiments administration of the CLL1-specific peptide ligands is local, e.g., directly into the bone marrow or intratumorally.

ii. Dosing

The CLL1-specific peptide ligands can be administered for prophylactic and/or therapeutic treatments. In therapeutic applications, compositions comprising the CLL1-specific peptide ligands are administered to a patient suffering from or at risk of developing leukemia in an amount sufficient to cure or at least partially arrest the disease and its complications, e.g., by eliminating or reducing the number of leukemic stem cells and/or preventing their proliferation and/or growth. An amount adequate to accomplish this is defined as a "therapeutically effective dose." Amounts effective for this use will depend upon the severity of the disease and the general state of the patient's health, and clinical studies are often done to determine the best dose for a given cancer type. An effective amount of the compound is that which provides either subjective relief of a symptom(s) or an objectively identifiable improvement as noted by the clinician or other qualified observer.

In prophylactic applications, compositions containing the CLL1-specific peptide ligands are administered to a patient not already in a disease state to prevent the onset of disease. Such an amount is defined to be a "prophylactically effective dose." In this use, the precise amounts again depend upon the patient's state of health.

Determination of an effective amount is well within the capability of those skilled in the art, especially in light of the detailed disclosure provided herein. Generally, an efficacious or effective amount of a combination of one or more polypeptides of the present invention is determined by first administering a low dose or small amount of a polypeptide or composition and then incrementally increasing the administered dose or dosages, adding a second or third medication as needed, until a desired effect of is observed in the treated subject with minimal or no toxic side effects. Applicable methods for determining an appropriate dose and dosing schedule for administration of a combination of the present invention are described, for example, in Brunton, et al., *Goodman and Gilman's The Pharmacological Basis of Therapeutics, Twelfth Edition,* 2010, McGraw-Hill Professional; in a Physicians' Desk Reference (PDR), 65$^{th}$ Edition, 2011; in *Remington: The Science and Practice of Pharmacy,* 21$^{st}$ Ed., 2006, supra; and in *Martindale: The Complete Drug Reference,* Sweetman, 2005, London: Pharmaceutical Press., and in Martindale, *Martindale: The Extra Pharmacopoeia,* 31st Edition., 1996, Amer Pharmaceutical Assn, each of which are hereby incorporated herein by reference.

Exemplary doses of the pharmaceutical formulations described herein, include milligram or microgram amounts of the CLL1-specific peptide ligands per kilogram of subject or sample weight (e.g., about 1 microgram per-kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of the CLL1-specific peptide ligands depend upon the potency of the composition with respect to the desired effect to be achieved. When the CLL1-specific peptide ligands are to be administered to a mammal, a physician, veterinarian, or researcher may, for example, prescribe a relatively low dose at first, subsequently increasing the dose until an appropriate response is obtained. In addition, it is understood that the specific dose level for any particular mammal subject will depend upon a variety of factors including the activity of the specific composition employed, the age, body weight, general health, gender, and diet of the subject, the time of administration, the route of administration, the rate of excretion, any drug combination, and the degree of expression or activity to be modulated.

The appropriate dosage of the polypeptides of the present invention will vary according to several factors, including the chosen route of administration, the formulation of the composition, patient response, the severity of the condition, the subject's weight, and the judgment of the prescribing physician. The dosage can be increased or decreased over time, as required by an individual patient. Usually, a patient initially is given a low dose, which is then increased to an efficacious dosage tolerable to the patient.

The dosage of CLL1-specific peptide ligands administered is dependent on the species of warm-blooded animal (mammal), the body weight, age, individual condition, surface area of the area to be treated and on the form of administration. The size of the dose also will be determined by the existence, nature, and extent of any adverse effects that accompany the administration of a particular compound in a particular subject. A unit dosage for administration to a mammal of about 50 to 70 kg may contain between about 5 and 500 mg of the active ingredient. Typically, a dosage of the CLL1-specific peptide ligands, is a dosage that is sufficient to achieve the desired effect.

Optimum dosages, toxicity, and therapeutic efficacy of compositions can further vary depending on the relative potency of individual compositions and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Compositions that exhibit large therapeutic indices are preferred. While compositions that exhibit toxic side effects can be used, care should be taken to design a delivery system that targets such compositions to the site of affected tissue to minimize potential damage to normal cells and, thereby, reduce side effects.

The data obtained from, for example, animal studies (e.g., rodents and monkeys) can be used to formulate a dosage range for use in humans. The dosage of polypeptides of the present invention lies preferably within a range of circulating concentrations that include the $ED_{50}$ with little or no toxicity. The dosage can vary within this range depending upon the dosage form employed and the route of administration. For any composition for use in the methods of the invention, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC).

In general, the dose equivalent of a polypeptide or composition, is from about 1.0 ng/kg to 100 mg/kg for a typical subject. A typical polypeptide composition of the present invention for intravenous administration would be about 1 ng/kg to 100 mg/kg per patient per day, for example, about 1.0 μg/kg to 10 mg/kg per patient per day. In various embodiments, dosages from about 10 μg/kg to 1.0 mg/kg per patient per day may be used. Actual methods for preparing administrable compositions will be known or apparent to those skilled in the art and are described in more detail in such publications as *Remington: The Science and Practice of Pharmacy,* 21$^{st}$ Ed., 2006, Lippincott Williams & Wilkins.

In one embodiment of the present invention, a pharmaceutical formulation of the present invention is administered, e.g., in a daily dose in the range from about 1 ng of compound per kg of subject weight (1 ng/kg) to about 100 mg/kg. In another embodiment, the dose is a dose in the range of about 1.0 μg/kg to about 50 mg/kg. In yet another embodiment, the dose is about 10 μg/kg to about 25 mg/kg. In another embodiment, the dose is about 25 μg/kg to about 15 mg/kg.

Exemplary doses of the pharmaceutical formulations can include 100-500 mg daily doses as needed. Pharmaceutical formulations can be administered at a concentration of about 25 mg/mL to about 50 mg/mL. Exemplary doses of the pharmaceutical formulations can include about 5-20 mg/kg, for example, about 10 mg/kg daily doses.

In embodiments involving the administration of the CLL1-specific binding peptides conjugated to a nanoparticle encapsulating a therapeutic agent (e.g., a chemotherapeutic agent), the decorated and loaded nanoparticle can be administered at a dose in the range of about 5 mg/kg to about 200 mg/kg, for example, at a dose in the range of about 10 mg/kg to about 100 mg/kg, for example at a dose of about 5, 10, 15, 25, 50, 75, 100, 150 or 200 mg/kg. Because the decorated nanoparticles are targeted to LSCs by the conjugated CLL1-specific binding peptides doses of encapsulated chemotherapeutic agent can be higher than if the chemotherapeutic agents were administered alone (e.g., not encapsulated in the nanoparticle). In some embodiments, the doses of nanoparticle-encapsulated chemotherapeutic agent are 1-fold, 2-fold, 3-fold, 4-fold, or more, in comparison to doses of the same chemotherapeutic agent administered without encapsulation in the nanoparticle. Doses of unencapsulated chemotherapeutic agents are known in the art. See, e.g., Brunton, et al., *Goodman and Gilman's The Pharmacological Basis of Therapeutics, Twelfth Edition,* 2010, McGraw-Hill Professional and Physicians' Desk Reference (PDR), 65$^{th}$ Edition, 2011.

Following successful treatment, it may be desirable to have the subject undergo maintenance therapy to prevent the recurrence of the disease or malignant condition treated.

iii. Scheduling

Dosing schedules can be calculated from measurements of polypeptides in the body of a subject. In general, dosage is from 1 ng to 1,000 mg per kg of body weight and may be given once or more daily, semiweekly, weekly, biweekly, semimonthly, monthly, bimonthly or yearly, as needed or appropriate. Persons of ordinary skill in the art can easily determine optimum dosages, dosing methodologies and repetition rates. One of skill in the art will be able to determine optimal dosing for administration of a polypeptide or polypeptide composition of the present invention to a human being following established protocols known in the art and the disclosure herein.

Single or multiple administrations of the pharmaceutical formulations may be administered depending on the dosage and frequency as required and tolerated by the patient. In any event, the composition should provide a sufficient quantity of the polypeptides of this invention to effectively treat the patient. Preferably, the dosage is administered once but may be applied periodically until either a therapeutic result is achieved or until side effects warrant discontinuation of therapy. Generally, the dose is sufficient to treat or ameliorate symptoms or signs of disease without producing unacceptable toxicity to the patient.

The daily dose can be administered once per day or divided into subdoses and administered in multiple doses, e.g., twice, three times, or four times per day. However, as will be appreciated by a skilled artisan, compositions described herein may be administered in different amounts and at different times. The skilled artisan will also appreciate that certain factors may influence the dosage and timing required to effectively treat a subject, including but not limited to the severity of the disease or malignant condition, previous treatments, the general health and/or age of the subject, and other diseases present. Moreover, treatment of a subject with a therapeutically effective amount of a composition can include a single treatment or, preferably, can include a series of treatments.

Thus, a pharmaceutical formulation thereof for intravenous administration would be about 0.01 to 100 mg/kg per patient per day. Dosages from 0.1 up to about 1000 mg/kg per patient per day may be used, particularly when the drug is administered to a secluded site and not into the blood stream, such as into a body cavity or into a lumen of an organ. Actual methods for preparing parenterally administrable compositions will be known or apparent to those skilled in the art and are described in more detail in such publications as *Remington: The Science and Practice of Pharmacy,* 21$^{st}$ Ed., 2006, Lippincott Williams & Wilkins.

To achieve the desired therapeutic effect, pharmaceutical formulations may be administered for multiple days at the therapeutically effective daily dose. Thus, therapeutically effective administration of compositions to treat a disease or malignant condition described herein in a subject may require periodic (e.g., daily) administration that continues for a period ranging from three days to two weeks or longer. Typically, compositions will be administered for at least three consecutive days, often for at least five consecutive days, more often for at least ten, and sometimes for 20, 30, 40 or more consecutive days, or longer, as needed. While consecutive daily doses are a preferred route to achieve a therapeutically effective dose, a therapeutically beneficial effect can be achieved even if the compounds or compositions are not administered daily, so long as the administration is repeated frequently enough to maintain a therapeutically effective concentration of the composition in the subject. For example, one can administer a composition every other day, every third day, or, if higher dose ranges are employed and tolerated by the subject, once a week.

c. Combination Therapies with Established Anticancer Therapies i. Chemotherapy

The CLL1-specific peptide ligands described herein can be co-administered with other agents as combination therapies.

Examples of chemotherapeutic agents that can be co-administered with the CLL1-specific peptide ligands include without limitation alkylating agents (cisplatin, carboplatin, and oxaliplatin); anti-metabolites (purine or pyrimidine mimetics including for example azathioprine and mercaptopurine); plant alkaloids and terpenoids (vinca alkaloids and taxanes); vinca alkaloids (vincristine, vinblastine, vinorelbine, and vindesine); podophyllotoxin (including etoposide and teniposide); taxanes (paclitaxel, taxol and docetaxel); topoisomerase inhibitors (Type I inhibitors: camptothecins, irinotecan and topotecan; Type II Inhibitors: amsacrine, etoposide, etoposide phosphate, and teniposide); antineoplastics (cytarabine (ara-C), daunorubicin, idarubicin, dactinomycin, doxorubicin, epirubicin, fludarabine and bleomycin). Any chemotherapeutic agent being used to treat the cancer of interest can be co-administered in a combination therapy regime with the CLL1-specific peptide ligands.

ii. Radiation

The CLL1-specific peptide ligands can be administered in conjunction with radiological procedures. A variety of radiological procedures are available for disease treatments. Any of the procedures know by one of skill can be combined with the polypeptides of the present invention for treatment of a patient. Radiological procedures comprise treatment using radiation therapy to damage cellular DNA. The damage to the cellular DNA can be caused by a photon, electron, proton, neutron, or ion beam directly or indirectly ionizing the atoms which make up the DNA chain. Indirect ionization occurs due to the ionization of water, forming free radicals, notably hydroxyl radicals, which then subsequently damage the DNA. In the most common forms of radiation therapy, the majority of the radiation effect is through free radicals.

Due to cellular DNA repair mechanisms, using agents that induce double-strand DNA breaks, such as radiation therapies, has proven to be a very effective technique for cancer therapy. Cancer cells are often undifferentiated and stem cell-like, such cells reproduce more rapidly and have a diminished ability to repair sub-lethal damage compared healthy and more differentiated cells. Further, DNA damage is inherited through cell division, leading to an accumulation of damage to the cancer cells, inducing slower reproduction and often death.

The amount of radiation used in radiation therapy procedure is measured in gray (Gy), and varies depending on the type and stage of cancer being treated and the general state of the patient's health. The dosage range can also be affected by cancer type, for example, the typical curative dosage for a solid epithelial tumor ranges from 60 to 80 Gy, while the dosage for lymphoma ranges from 20 to 40 Gy.

Preventative (adjuvant) doses can also be employed and typically range from 45 to 60 Gy administered in 1.8 to 2 Gy fractions (e.g., for breast, head and neck cancers). Many other factors are well-known and would be considered by those of skill when selecting a dose, including whether the patient is receiving other therapies (such as for example, but not limited to administration of the CLL1-specific peptide ligands, administration of chemotherapies and the like), patient co-morbidities, timing of radiation therapy (for example, whether radiation therapy is being administered before or after surgery), and the degree of success of any surgical procedures.

Delivery parameters of a prescribed radiation dose can be determined during treatment planning by one of skill. Treatment planning can be performed on dedicated computers using specialized treatment planning software. Depending on the radiation delivery method, several angles or sources may be used to sum to the total necessary dose. Generally, a plan is devised that delivers a uniform prescription dose to the tumor and minimizes the dosage to surrounding healthy tissues.

iii. Surgery

The CLL1-specific peptide ligands can be administered in conjunction with surgical removal or debulking of tumors, e.g., bone marrow transplantation. Any of the procedures known by one of skill can be combined with the administration of the CLL1-specific peptide ligands of the present invention for treatment and/or prevention of leukemia in a patient.

6. Methods of Monitoring Efficacy

A variety of methods can be employed in determining efficacy of therapeutic and prophylactic treatments with the CLL1-specific peptide ligands described herein. Generally, efficacy is the capacity to produce an effect without significant toxicity. Efficacy indicates that the therapy provides therapeutic or prophylactic effects for a given intervention (examples of interventions can include by are not limited to administration of a pharmaceutical formulation, employment of a medical device, or employment of a surgical procedure). Efficacy can be measured by comparing treated to untreated individuals or by comparing the same individual before and after treatment. Efficacy of a treatment can be determined using a variety of methods, including pharmacological studies, diagnostic studies, predictive studies and prognostic studies. Examples of indicators of efficacy include but are not limited to inhibition of tumor cell growth and promotion of tumor cell death.

The efficacy of an anti-cancer treatment can be assessed by a variety of methods known in the art. The CLL1-specific peptide ligands can be screened for prophylactic or therapeutic efficacy in animal models in comparison with untreated or placebo controls. The CLL1-specific peptide ligands identified by such screens can be then analyzed for the capacity to induce tumor cell death or enhanced immune system activation. For example, multiple dilutions of sera can be tested on tumor cell lines in culture and standard methods for examining cell death or inhibition of cellular growth can be employed. (See, e.g., Maniatis, et al., *Molecular Cloning: A Laboratory Manual*, Cold Spring Harbor Lab., New York, 1982; Ausubel, et al. Editor, *Current Protocols in Molecular Biology*, USA, 1984-2008; and Ausubel, et al. Editor, *Current Protocols in Molecular Biology*, USA, 1984-2008; Bonifacino, et al., Editor, *Current Protocols in Cell Biology*, USA, 2010; all of which are incorporated herein by reference in their entirety.)

The methods of the present invention provide for detecting inhibition disease in patient suffering from or susceptible to various cancers. A variety of methods can be used to monitor both therapeutic treatment for symptomatic patients and prophylactic treatment for asymptomatic patients.

Monitoring methods can entail determining a baseline value of a tumor burden and/or the presence of leukemic stem cells (LSCs) in a patient before administering a dosage of the CLL1-specific peptide ligands, and comparing this with a value for the tumor burden and/or the presence of leukemic stem cells (LSCs) after treatment, respectively.

With respect to therapies using the CLL1-specific peptide ligands, a significant decrease (e.g., greater than the typical margin of experimental error in repeat measurements of the same sample, expressed as one standard deviation from the mean of such measurements) in value of the tumor burden and/or the presence of leukemic stem cells (LSCs) signals a positive treatment outcome (e.g., that administration of the CLL1-specific peptide ligands has blocked or inhibited, or reduced progression of tumor and/or LSC growth and/or metastasis). In some embodiments, treatment with the CLL1-specific peptide ligands is considered to be efficacious if the tumor burden and/or the presence of leukemic stem cells (LSCs) in the subject being treated is reduced by at least about 10%, for example, by at least about 20%, 30%, 40% or 50%, or by completely eliminating the tumor burden and/or the presence of leukemic stem cells (LSCs), e.g., comparing tumor burden and/or the presence of leukemic stem cells (LSCs) before and after treatment in the subject.

In other methods, a control value of tumor burden and/or the presence of leukemic stem cells (LSCs) (e.g., a mean and standard deviation) is determined from a control population of individuals who have undergone treatment with the CLL1-specific peptide ligands. Measured values of tumor burden and/or the presence of leukemic stem cells (LSCs) in a patient are compared with the control value. If the measured level in a patient is not significantly different (e.g., more than one standard deviation) from the control value, treatment can be discontinued. If the tumor burden level and/or the leukemic stem cell (LSC) level in a patient is significantly above the control value, continued administration of agent is warranted.

In other methods, a patient who is not presently receiving treatment but has undergone a previous course of treatment is monitored for tumor burden and/or the presence of leukemic stem cells (LSCs) to determine whether a resumption of treatment is required. The measured value of tumor burden and/or the presence of leukemic stem cells (LSCs) in the patient can be compared with a value of tumor burden and/or the presence of leukemic stem cells (LSCs) previously achieved in the patient after a previous course of treatment. A significant decrease in tumor burden and/or the presence of leukemic stem cells (LSCs) relative to the previous measurement (e.g., greater than a typical margin of error in repeat measurements of the same sample) is an indication that treatment can be resumed. Alternatively, the value measured in a patient can be compared with a control value (mean plus standard deviation) determined in a population of patients after undergoing a course of treatment. Alternatively, the measured value in a patient can be compared with a control value in populations of prophylactically treated patients who remain free of symptoms of disease, or populations of therapeutically treated patients who show amelioration of disease characteristics. In all of these cases, a significant increase in tumor burden and/or the presence of leukemic stem cells (LSCs) relative to the control level (e.g., more than a standard deviation) is an indicator that treatment should be resumed in a patient.

The tissue sample for analysis is typically blood, bone marrow or lymph node from the patient. The sample can be analyzed for indication of neoplasia. Neoplasia or tumor burden and/or the presence of leukemic stem cells (LSCs) can be detected using any method known in the art, e.g., visual observation of a biopsy by a qualified pathologist, or other visualization techniques, e.g., radiography, ultrasound, magnetic resonance imaging (MRI).

7. Methods of Diagnosis a. Patients Subject to Diagnosis

The binding of the CLL1-specific peptide ligands find use in the detection and diagnosis of leukemia, particularly acute myelogenous leukemia (AML), in a subject. In some embodiments, the subject may have or be at risk of developing a subtype of AML, including, e.g., minimally differentiated acute myeloblastic leukemia (M0), acute myeloblastic leukemia, without maturation (M1), acute myeloblastic leukemia, with granulocytic maturation (M2), promyelocytic, or acute promyelocytic leukemia (APL) (M3), acute myelomonocytic leukemia (M4), myelomonocytic together with bone marrow eosinophilia (M4eo), acute monoblastic leukemia (M5a), acute monocytic leukemia (M5b), acute erythroid leukemias, including erythroleukemia (M6a), pure erythroid leukemia (M6b), acute megakaryoblastic leukemia (M7), or acute basophilic leukemia (M8). The present CLL1-specific ligands can bind to CLL1, on the surface of a cell. The binding levels of the CLL1-specific peptide ligands can be determined on leukemic stem cells. To determine whether the CLL1-specific peptide ligands bind to LSCs, a biological sample, e.g, blood or bone marrow, may be taken.

Accordingly, patients who can benefit from the present methods may already present with symptoms of leukemia. For example, evidence of leukemia may be present (by visual inspection or palpation (e.g., of lymph nodes, spleen and/or liver), testing of white blood cell populations, or by scanning techniques, e.g., magnetic resonance imaging (MRI) or Positron Emission Tomography (PET) scans).

The present diagnostic methods find use in conjunction with presently available diagnostic tests for leukemia, particularly AML. The patient may already have a preliminary diagnosis of leukemia, e.g., based on elevated white blood cell count and other symptoms and/or diagnostic parameters known in the art. In such cases, obtaining a biological sample, e.g., from blood, bone marrow and/or a lymph node, may be justified and detection of the binding levels of the CLL1-specific peptide ligands or the expression levels of CLL1 on the surface of cells suspected of being cancerous can confirm or contradict a preliminary diagnosis of leukemia, particularly AML, mediated at least in part by surface expression of CLL1.

In other cases, the patient may have a personal or familial history of leukemia or a cancer of another tissue origin. For example, the patient may be in remission following successful therapeutic treatment of the leukemia. The patient may also have tested positive for a gene associated with increased risk of leukemia or the recurrence of leukemia. In various embodiments, the subject is an adult, a juvenile or a child.

b. Obtaining a Biological Sample

The biological sample from which the expression levels are measured will depend on the tissue suspected on being cancerous. Usually, the biological sample is from the tissue suspected of being cancerous and/or suspected of containing leukemic stem cells, e.g., blood, bone marrow, lymph node.

In some embodiments, the biological sample is from a biopsy, e.g., bone marrow or lymph node. In certain instances, for example, the determination of the presence of cancer metastasis, it may be appropriate for the biological sample to be from a tissue other than blood, bone marrow or lymph node. In some embodiments, it may be appropriate to measure the presence of CLL1-specific peptide ligand binding levels in a tissue different from the tissue suspected of being cancerous, e.g., to determine the presence of metastasis.

c. Determining the Presence of Cancer

The level of binding of the CLL1-specific peptide ligands can be measured according to methods well known in the art, and described herein. The level of peptide ligand binding can be detected, for example, using directly or indirectly labeled detection agents, e.g., fluorescently, radioactively or enzymatically labeled CLL1-specific peptide ligands. For example, the peptides can be conjugated to labeled beads, e.g., beads that can be detected via a fluorescent label, a chemiluminescent label, a quantum dot label, or any other label known in the art. Assays using labeled beads are well known in the art.

To provide an illustrative example, a blood, bone marrow, or lymph node tissue sample is obtained from the subject. The blood, bone marrow or lymph node cells are then contacted with a CLL1-specific peptide ligand, as described herein. The peptides can be directly labeled, e.g., by conjugation or attachment to a labeled bead. For example, the bead can be labeled with a fluorophore, a chemiluminescent moiety or a quantum dot, or any other detectable label. Peptides conjugated to a bead facilitate detection of binding of the peptide ligands to cancer cells in the blood, bone marrow or lymph node sample and concentration of cancer cells bound to the peptide ligands. The presence of labeled cells can then be detected and quantified. For example, cells coated with beads conjugated to a CLL1-specific peptide ligand can be detected using a microscope or by flow cytometry.

In some embodiments, the CLL1-specific ligands are linked (e.g., via chemical linkage or fusion) to a known epitope for antibody binding (e.g., immunoglobulin Fc, FLAG-tag or c-myc epitopes). Peptide ligands alone or linked to an antibody epitope can be measured using immunoassays known in the art, including immunohistochemical staining, Western blotting, ELISA and the like with an antibody that selectively binds to antibody epitope or a fragment thereof. Detection of peptides using antibodies in immunoassays is known in the art (see, e.g., Harlow & Lane, *Using Antibodies: A Laboratory Manual* (1998); Coligan, et al., eds., *Current Protocols in Immunology* (1991-2010); Goding, *Monoclonal Antibodies: Principles and Practice* (3rd ed. 1996); and Kohler & Milstein, *Nature* 256:495-497 (1975).

Binding levels of the CLL1-specific peptide ligands to LSCs can be detected using any method known in the art. Exemplary methods include flow cytometry, tissue lysate detection, Western immunoblot and immunohistochemistry.

To provide an illustrative example, a blood, bone marrow or lymph node tissue sample (e.g., a biopsy) is incubated with an antibody that specifically binds to the CLL1-specific peptide ligand, alone or linked to an epitope tag, under conditions (e.g., time, temperature, concentration of sample) sufficient to allow specific binding. The tissues optionally can be fixed (e.g., in formaldehyde) and permeabilized prior to incubation with antibody. The anti-peptide antibodies can be exposed to a tissue sample for about 0.5, 1.0, 1.5, 2.0, 2.5, 3.0 hours, or overnight, about 8, 10 or 12 hours, as appropriate. However, incubation time can be more or less depending on, e.g., the composition of the antigen, the dilution of the sample and the temperature for incubation. Incubations using less diluted samples and higher temperatures can be carried out for shorter periods of time. Incubations are usually carried out at room temperature (about 25° C.) or at biological temperature (about 37° C.), and can be carried out in a refrigerator (about 4° C.). Washing to remove unbound sample before addition of a secondary antibody is carried according to known immunoassay methods.

The CLL1-specific peptide ligands can be directly labeled or labeled secondary antibodies can be used to detect antibodies in a sample that have bound to the peptide ligands. Secondary antibodies bind to the constant or "C" regions of different classes or isotypes of immunoglobulins—IgM, IgD, IgG, IgA, and IgE. Usually, a secondary antibody against an IgG constant region is used in the present methods. Secondary antibodies against the IgG subclasses, for example, IgG1, IgG2, IgG3, and IgG4, also find use in the present methods. Secondary antibodies can be labeled with any directly or indirectly detectable moiety, including a fluorophore (e.g., fluoroscein, phycoerythrin, quantum dot, Luminex bead, fluorescent bead), an enzyme (e.g., peroxidase, alkaline phosphatase), a radioisotope (e.g., $^{3}H$, $^{32}P$, $^{125}I$, $^{123}I$, $^{11}C$, $^{13}N$, $^{15}O$, $^{82}Rb$, technetium-99m (Tc-99m), thallium-201) or a chemiluminescent moiety. Labeling signals can be amplified using a complex of biotin and a biotin binding moiety (e.g., avidin, streptavidin, neutravidin). Fluorescently labeled anti-human IgG antibodies are commercially available from Molecular Probes, Eugene, Oreg. Enzyme-labeled anti-human IgG antibodies are commercially available from Sigma-Aldrich, St. Louis, Mo. and Chemicon, Temecula, Calif.

The method of detection of the levels of binding of the CLL1-specific peptide ligands in a sample will correspond with the choice of label of the secondary antibody. For example, if tissue lysates containing bound to the peptide ligands are transferred onto a membrane substrate suitable for immunoblotting, the detectable signals (e.g., blots) can be quantified using a digital imager if enzymatic labeling is used or an x-ray film developer if radioisotope labeling is used. Likewise, tissue samples subject to immunohistochemistry can be evaluated using immunofluorescence microscopy or a scanning microscope and automated scanning software capable of detecting and quantifying fluorescent, chemiluminescent, and/or colorimetric signals. Such methods of detection are well known in the art and are described herein.

General immunoassay and immunohistochemical techniques are well known in the art. Guidance for optimization of parameters can be found in, for example, Wu, *Quantitative Immunoassay: A Practical Guide for Assay Establishment, Troubleshooting, and Clinical Application*, 2000, AACC Press; *Principles and Practice of Immunoassay*, Price and Newman, eds., 1997, Groves Dictionaries, Inc.; *The Immunoassay Handbook*, Wild, ed., 2005, Elsevier Science Ltd.; Ghindilis, Pavlov and Atanassov, *Immunoassay Methods and Protocols*, 2003, Humana Press; Harlow and Lane, *Using Antibodies: A Laboratory Manual*, 1998, Cold Spring Harbor Laboratory Press; *Immunoassay Automation: An Updated Guide to Systems*, Chan, ed., 1996, Academic Press; Dabbs, *Diagnostic Immunohistochemistry: Theranostic and Genomic Applications*, 2010, Saunders; Renshaw, *Immunohistochemistry: Methods Express Series*, 2007, Scion Publishing Ltd.; and Buchwalow and Böcker, *Immunohistochemistry: Basics and Methods*, 2010, Springer.

The presence of binding or of increased binding of the CLL1-specific peptide ligands is indicated by a detectable signal (e.g., a blot, fluorescence, chemiluminescence, color, radioactivity) in an immunoassay or immunohistochemical assay, where the biological sample from the patient is contacted with antibody or antibody fragment that specifically binds to the peptide ligand or epitope tag.

Detectable signal can be compared to the signal from a normal or non-cancerous control sample (e.g., from blood, bone marrow or lymph node) to a threshold value. In some embodiments, the presence of binding or of increased binding of the CLL1-specific peptide ligands is detected, and the presence or increased risk of cancer is indicated, e.g., when the detectable signal of peptide ligand binding levels in the test sample is at least about 10%, 20%, 30%, 50%, 75% greater in comparison to the signal of peptide ligand binding levels in the normal or non-cancerous control sample or the predetermined threshold value. In some embodiments, an increased binding level of the CLL1-specific ligand is detected, and the presence or an increased risk of cancer is indicated, when the detectable signal of CLL1-specific peptide ligand binding level in the test sample is at least about 1-fold, 2-fold, 3-fold, 4-fold or more, greater in comparison to the signal of CLL1-specific peptide ligand binding level in the normal or non-cancerous control sample or the predetermined threshold value. Usually, the sample and control or predetermined threshold levels are from the same tissue types.

In some embodiments, the CLL1-specific peptide ligand binding level is compared with CLL1-specific peptide ligand binding levels in a control tissue or control cells known to be cancerous. In this case, the CLL1-specific peptide ligand binding level in the test biological sample equivalent to or greater than the positive control sample, known to be cancerous, is indicative of cancer. Usually, the sample and control or predetermined threshold levels are from the same tissue types (e.g., blood, bone marrow or lymph node tissue).

Alternatively, if the CLL1-specific peptide ligand binding levels in the test biological sample are less than the CLL1-specific peptide ligand binding levels in the positive cancerous tissue control or the predetermined threshold level, then a diagnosis of cancer is generally not indicated. Likewise, if the CLL1-specific peptide ligand binding levels in the test biological sample are equivalent to or less than a normal or non-cancerous control or the predetermined threshold level, then a diagnosis of cancer is not indicated.

In some embodiments, the results of the CLL1-specific peptide ligand binding level determinations are recorded in a tangible medium. For example, the results of the present diagnostic assays (e.g., the observation of the presence or increased presence of CLL1-specific peptide ligand binding) and the diagnosis of whether or not the presence or an increased risk of cancer is determined can be recorded, e.g., on paper or on electronic media (e.g., audio tape, a computer disk, a CD, a flash drive, etc.).

In some embodiments, the methods further comprise the step of providing the diagnosis to the patient of whether or not there is the presence or an increased risk of cancer in the patient based on the results of the CLL1-specific peptide ligand binding level determinations.

In some embodiments, the methods further comprise the step of providing or recommending an appropriate course of treatment to the patient based on the results of the CLL1-specific peptide ligand binding level determinations.

Methods of determining the presence of leukemia and/or CLL1-expressing leukemic stem cells in a subject based on the binding of the CLL1-specific peptide ligands described herein to a biological sample suspected of containing LSCs (e.g., blood, bone marrow and/or lymph node) can be performed in conjunction with other known methods of diagnosing leukemia.

8. Methods of In Situ Imaging

The CLL1-specific peptide ligands described herein find use in methods of local visualization of leukemic stem cells (LSCs), for example, which may be present in the blood, bone marrow and/or lymph nodes of a subject. A CLL1-specific peptide ligand conjugated to a detectable label, e.g., a fluorescent label, finds use for this application.

Another contemplated application of the CLL1-specific peptide ligands is imaging detection of LSCs that can supplement or decrease intrusive biopsies. Magnetic resonance imaging (MRI) and positron emission tomography (PET) can be performed in a subject suspected of having or known to have leukemia. Both MRI and PET scans have been widely used for the diagnosis of malignancies, and find use in the diagnosis and detection of leukemic malignancies. Therefore, MRI and PET or single photon emission computed tomography (SPECT) can be used to facilitate the detection of leukemia using the CLL1-specific peptide ligands described herein conjugated to imaging agents, for example, an iron oxide for MRI and a radioisotope for PET/SPECT (e.g., $^{123}I$, $^{11}C$, $^{13}N$, $^{15}O$, $^{18}F$, $^{82}Rb$, technetium-99m (Tc-99m), thallium-201).

In order to allow for in situ imaging, the CLL1 specific peptide ligands attached to an appropriate imaging agent are contacted with the tissue suspected of containing or known to contain leukemic stem cells (LSCs) within the subject (e.g., blood, bone marrow, lymph node). By performing an appropriate imaging methodology on the patient, the location and extent of LSCs in the imaged tissue can be determined.

In some embodiments, the methods further comprise removing, resecting or excising the LSCs from the tissue, e.g., based on detecting the binding of the CLL1-specific peptide ligands. Magnetic particles conjugated to a CLL1-specific peptide ligand can further be used for the extraction and removal of LSCs. Use of magnetic nanoparticle-peptide conjugates for the in vitro and in vivo targeting and extraction of cancer cells is described, e.g., in Scarberry, et al., *J Am Chem Soc* (2008) 130(31):10258-10262.

9. Kits

The present invention also provides for kits comprising a CLL1-specific peptide ligand, as described herein. The embodiments of the CLL1-specific peptide ligand in the kits are as described herein. In some embodiments, the CLL1-specific peptide ligand is conjugated to or attached to a labeled bead.

In addition the kits will typically include instructional materials disclosing means of use of the CLL1-specific peptide ligand. In the kits, the CLL1-specific ligands may be formulated for administration, and provided in one or multiple unit doses. The kits may also include additional components to facilitate the particular application for which the kit is designed. The kits may additionally include buffers and other reagents routinely used for the practice of a particular method. Such kits and appropriate contents are well known to those of skill in the art.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

EXAMPLES

The following examples are offered to illustrate, but not to limit the claimed invention.

Example 1

Methods
Identification of Ligands Targeting CLL1

The CLL1 cDNA expression vector was purchased from the American Type Culture Collection (Manassas, Va., USA) and was subcloned to a pcDNA3.1 expression vector. The C7C phage display peptide library was purchased from the New England Biolab (Ipswich, Mass., USA). CLL1 was expressed in 5637 (bladder transitional cell carcinoma), A549 (non-small cell lung cancer) and HTB38 (colon cancer) cells for sequential panning to identify peptides that bind to CLL1. No commercially available anti-CLL1 antibody to detect the expression of CLL1 was available. Therefore, the CLL1-RFP (red fluorescence protein) chimeric gene was constructed, and cloned into the pcDNA3.1 expression vector in which RFP replaced part of the intracellular domain of CLL1 to allow the monitoring of CLL1 expression. To eliminate any phage and peptides that may bind to the confounding cells in vivo, the C7C library was subtracted with whole blood, peripheral blood mononuclear cells (PBMC), normal healthy hematopoietic stem cells left over from allogeneic stem cell transplantation, human umbilical vascular endothelial cells (HUVEC), fibroblasts, 5637, A549 and HTB38 cells, for 4-6 hours with each cell type, before each round of panning (FIG. 1A). The subtracted phage library was then sequentially panned against 5637, A549 and HTB38 cells expressing CLL1-RFP per manufacturer's protocol. The library was panned against three different cancer cell types in order to minimize the possibility of isolating artifactual peptides that bind to intrinsic surface molecules on cells other than CLL1. Each round of panning was performed for only one hour to select those peptides with high affinity to CLL1. After three rounds of panning, 36 clones were selected, amplified and submitted for sequencing. The amino acid sequences were aligned for comparison (Table 1).

TABLE 1

(SEQ ID NOS 23, 17 and 25-33, respectively, in order of appearance)

| Sequences of Amino acids | Number of clones (total: 36 clones) |
| --- | --- |
| CPLRSAAAC | 11 |
| CDLRSAAVC | 7 |

TABLE 1-continued (SEQ ID NOS 23, 17 and 25-33, respectively,
in order of appearance)

| Sequences of<br>Amino acids | Number of clones<br>(total: 36 clones) |
|---|---|
| CLLRTAAVC | 3 |
| CLLRSAAVC | 1 |
| CTLRTAAVC | 1 |
| CALRSAAVC | 1 |
| CVLRSSGPC | 5 |
| CSLRSSGPC | 3 |
| CPLRSSGPC | 2 |
| CTLRSSGPC | 1 |
| CPTPPFSFC | 1 |

Figure 1B:
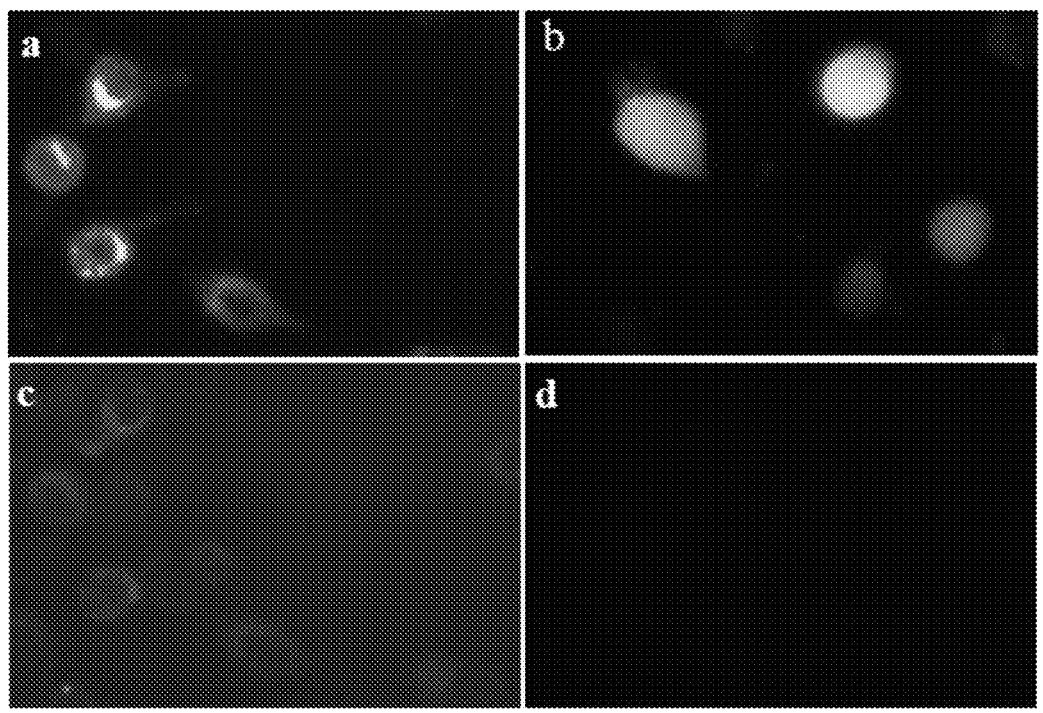
Figure 1C:
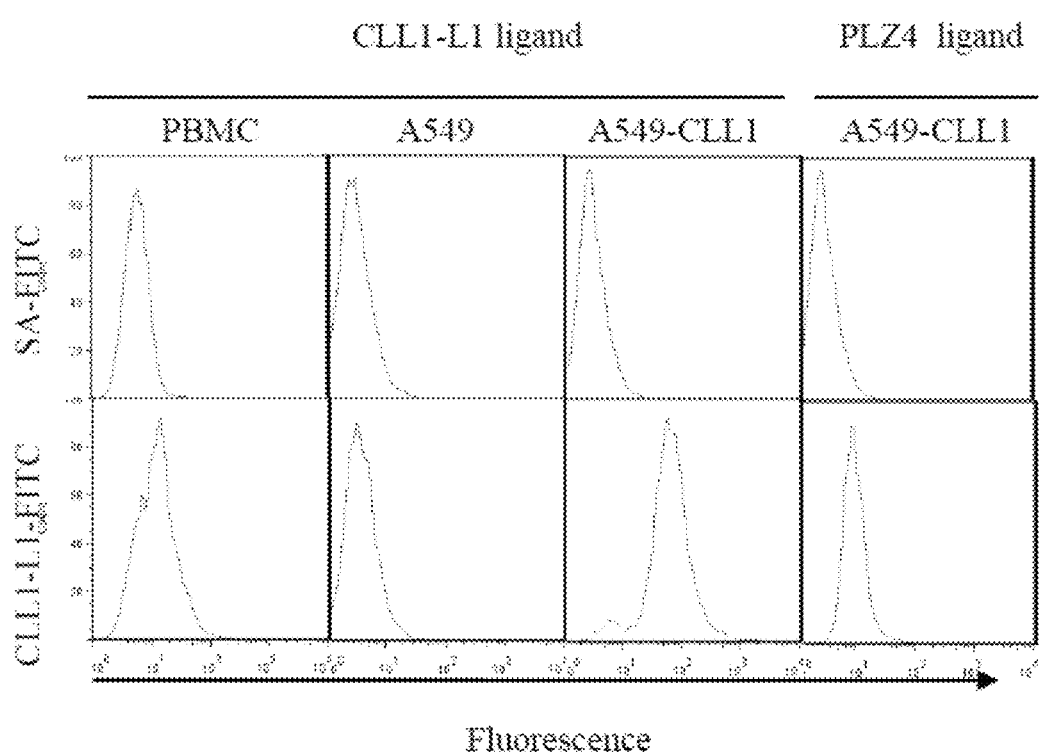
Figure 1D:
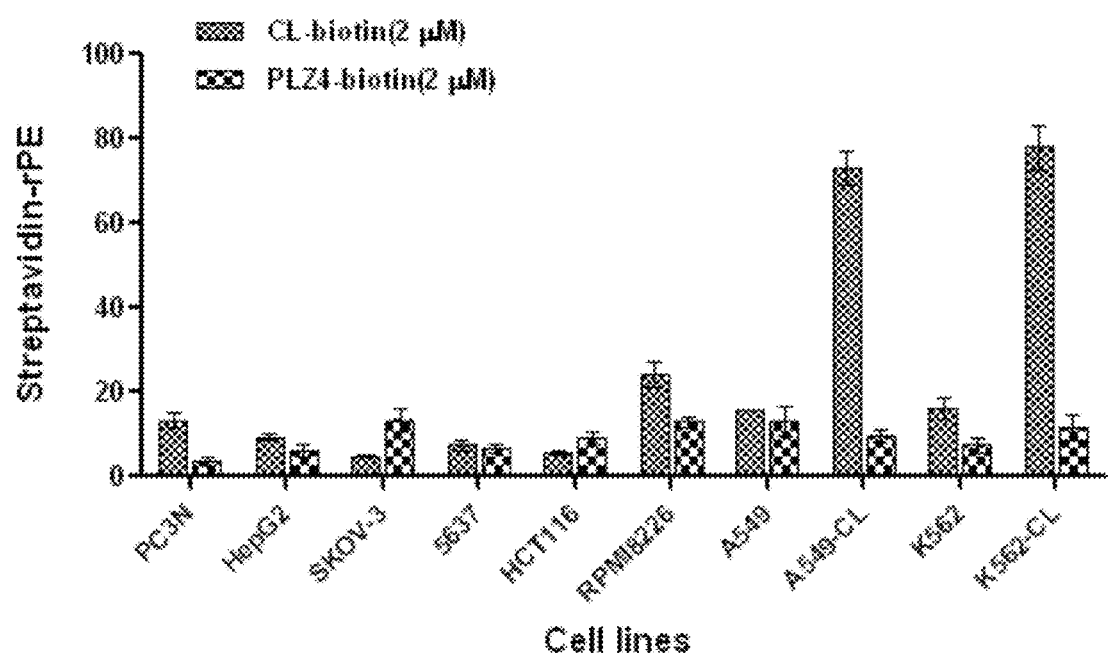

One peptide, CLL1-L1, with the sequence of CDLR-SAAVC (SEQ ID NO: 17) was synthesized for further analysis. To determine the binding specificity, cell lines purchased from the American Type Culture Collection (ATCC), such as PC3N (Prostate), HepG2 (Liver), Skov-3 (Ovarian), 5637 (Bladder), HCT-116 (Colon), RPMI8226 (Myeloma), A549 (Lung), K562 (Leukemia), A549 and K562 cells, both expressing CLL1, were incubated with CLL1-L1 conjugated to biotin and probed with streptavidin-phycoerythrin (PE) (excitation 480 nm, emission 578 nm) (FIG. 1D). A bladder cancer-specific ligand, PLZ4, conjugated to biotin was used as the negative control.

Synthesis of Targeting and Non-Targeting Nanomicelles

The methodology to synthesize CLL1-targeting peptides has been published [Lam, et al., *Nature* (1991) 354:82-84; Lam, et al., *Chem Rev* (1997) 97:411-448; and Zhang, et al., *Urol Oncol* (2011) PMID:20888272]. In brief, an (Alloc) lysine(Fmoc) was coupled onto Rink amide resin in order to introduce anchor groups (alkyne) for the post-cleavage coupling of CLL1 targeting peptides to the telodendrimer molecule. The peptides were synthesized on the lysine (Alloc)-Rink resin sequentially via Fmoc peptide chemistry [Chan W C, White P D: Fmoc Solid Phase Peptide Synthesis: A Practical Approach. Oxford, UK, Oxford University Press, 2000]. Then hexynoic acid was coupled onto lysine side chain after the treatment of resin with Pd(Ph3P)4 to remove Alloc group. After synthesis and cleavage of the lysine(alkyne)-peptide from the solid support, the crude peptide was treated with a buffer of air-saturated 50 mM ammonium bicarbonate in the presence of active charcoal, which resulted in formation of cyclized peptides via the oxidative coupling of the two cysteines located at the carboxy and amide termini of the peptide. The charcoal was removed by filtration and the solution was lyophilized. Crude peptide was purified by reverse-phase HPLC to at least 95% purity. The molecular weight of separated fractions was characterized by MALDI-TOF MS in order to confirm the peptide sequence. The purity of the resulting peptides was determined by analytical HPLC.

The details of synthesis of nanomicelles have been published [Xiao, et al., *Biomaterials* (2009) 30:6006-6016]. In brief, an azido acid was coupled onto free N-terminal of BocNH-PEG-NH2 via peptide chemistry. Then a dendritic polylysines was synthesized via Fmoc peptide chemistry and further capped with eight cholic acid (CA) via NHS ester chemistry. To determine the completeness of the coupling, the Kaiser test was performed [Kaiser, et al., *Anal Biochem* (1970) 34:595-598]. The final product was collected by ether precipitation and purified using the repeated dissolve-precipitate procedure in dichloromethane and cold ether to remove the coupling agents and impurities. The crude telodendrimer, a white powder, was dissolved in pure water and dialyzed against a large volume of water (MWCO of 3500 Dalton). The telodendrimer solution was then lyophilized to yield white powder. The polydispersity and molecular weight of the telodendrimer was characterized by Gel Permeation Chromatography (GPC) and MALDI-TOF Mass Spectrometry, and the chemical structure was characterized by nuclear magnetic resonance (NMR). The purity of the telodendrimer was measured by analytical HPLC. Aqueous-phase Click chemistry between azido and alkyne groups, catalyzed by cuprous ion, was used for coupling the alkyne group of CLL1-targeting peptides onto the azide groups at the end of PEG on telodendrimer. The purity of the CLL1-targeting telodendrimer was analyzed using HPLC, and the molecular weight was measured by MALDI-TOF MS. To load daunorubicin (DNR) or fluorescent dye DiI into nanomicelles, DNR and/or DiI are mixed with 20 mg of telodendrimer at different ratios, dissolved in chloroform (5 mL) in a 10 mL-flask. The chloroform was removed under vacuum on a rotary evaporator, and further dried under high vacuum for 30 min. One mL of USP saline was then added into the flask. The mixture was vortexed and sonicated for 30 min at room temperature. The final product was analyzed for drug loading capacity by HPLC analysis, and for nanomicelle size and polydispersity with a dynamic light scattering (DLS, Microtrac) particle sizer and transmission electron microscopy (TEM, Philips CM-120). It was filtered through a filter (0.22 µm) before injection into sterilized vials for further studies.

Uptake of Drug-Loaded Nanomicelles by Cells Expressing CLL1

Since the cytoplasm of adherent cells spreads wider and has a narrower focal plane than that of suspension AML cells, adherent A549 cells transfected with a CLL1 expression vector were used as a model system for easy visualization of nanomicelle-mediated drug delivery. The expression vector was constructed so that the cytoplasmic domain of CLL1 was replaced with green or red fluorescence protein (GFP or RFP) to monitor the expression of CLL1 by green or red fluorescence microscopy. To track the cellular uptake, nanomicelles were loaded with DiI, a red fluorescent dye (excitation: 549 nm, emission: 565 nm). A549 cells transfected with the GFP vector alone (control cells), or CLL1-GFP (experimental cells) were cultured in chamber slides overnight. Two types of DiI-loaded nanomicelles were used for this experiment: (1) non-targeting nanomicelles that were not decorated with CLL1-targeting peptides; and (2) targeting nanomicelles that were covalently coated with CLL1-targeting peptides. A549 cells expressing GFP or CLL1-GFP were incubated with these two types of nanomicelles for 10, 20, 30 and 60 minutes, and washed with complete culture medium three times to remove unbound nanomicelles. The cells were then examined by fluorescence microscopy.

To further demonstrate that the targeting nanomicelles penetrated into the CLL1-expressing cells, high-resolution live cell imaging was performed with a DeltaVision deconvolution imaging system (AppliedPrecision, WA, USA). A549 cells expressing GFP or expressing CLL1-GFP were cultured overnight on glass bottom culture dishes (MatTek, MA, USA), washed once with complete culture medium, and added with nontargeting or targeting nanomicelles (both were loaded with DiI dye, 0.4 mg/ml), respectively. Cells were incubated at 37° C. for 15 min, and washed three times with PBS buffer (pH 7.4). These dishes were then directly examined with the DeltaVision imaging system.

Targeting Efficacy of Clinical Specimens

Peripheral blood specimens from AML patients were drawn for this study after informed consent was obtained. This study was approved by the Institutional Review Board of the University of California Davis. Leukemic cells together with some normal PBMC were isolated using Ficoll gradient. These isolated cells then passed through CD34(+) MACS columns (Miltenyi, Bergisch Gladbach, Germany) to enrich CD34(+) leukemic cells. Over 96% of the isolated cells were CD34(+) cells. Normal hematopoietic stem cells were obtained from leftover allogeneic stem cell transplantation specimens. To determine the targeting efficiency of nanomicelles coated with CLL1-targeting peptides, enriched CD34(+) cells were incubated with different concentrations of nontargeting or targeting nanomicelles at 37° C. for 30 min. These cells were washed three times with PBS buffer (pH 7.4, 0.5% BSA), and the fluorescence density was detected by flow cytometry.

Results

Development of Ligands Targeting CLL1

The strategy of panning the PhD C7C phage peptide display library is shown in FIG. 1A. After panning, a total of 36 phage clones were sequenced. After alignment, two consensus sequences were identified: CXLR(S/T)AAVC (SEQ ID NO: 34) and CXLRSSGPC (SEQ ID NO: 24) (Table 1), in which "X" represents several amino acids that can be replaceable. Serine (S) and threonine (T) belong to the same hydrophilic class of amino acids with only one methyl group difference. Of these two major sequences, one common motif exists: "LR(S/T)". To confirm that these ligands indeed bind to CLL1, A549 cells were transfected with a CCL1-RFP expression vector (FIG. 1B panel a) or RFP (FIG. 1B panel b, the control). Expression of CLL1-RFP or RFP could be visualized by the appearance of red fluorescence. For subsequent in depth characterization, we selected the peptide CDLRSAAVC (SEQ ID NO: 17) instead of CPLRSAAAC (SEQ ID NO: 23) because aspartic acid (D) is more hydrophilic than proline (P), which makes the peptide more water soluble and easier to synthesize and manipulate. A549 cells expressing CCL1-RFP or RFP alone were incubated with phage displaying the CDLRSAAVC (SEQ ID NO: 17) peptide, and probed with anti-M13 monoclonal antibody-FITC conjugate. Phage expressing the CDLRSAAVC (SEQ ID NO: 17) peptide were detected on the surface of A549 cells expressing CLL1-RFP (FIG. 1B panel c), but not on cells expressing RFP (FIG. 1B panel d). This peptide is named CLL1-L1 and was used for all subsequent experiments. Flow cytometry studies were also performed to determine cell binding. CLL1-L1 was conjugated to biotin through the polyethylene glycol (PEG) linker. Cells were incubated with biotinylated CLL1-L1 and probed with streptavidin-PE. No significant binding of CLL1-L1 to PBMC and A549 control cells was observed while significant binding of CLL1-L1 to A549 cells expressing CLL1-GFP was detected (FIG. 1C).

To further determine the binding specificity, cell lines of various origins were probed with CLL1-L1 or a bladder cancer-specific ligand PLZ4 as a negative control. Specifically, CLL1-L1 bound to A549 and K562 cells that expressed recombinant CLL1, but not to the parental A549, K562 or other cell lines (FIG. 1D).

Development and Characterization of Nanomicelles Targeting CLL1

Figure 2A:
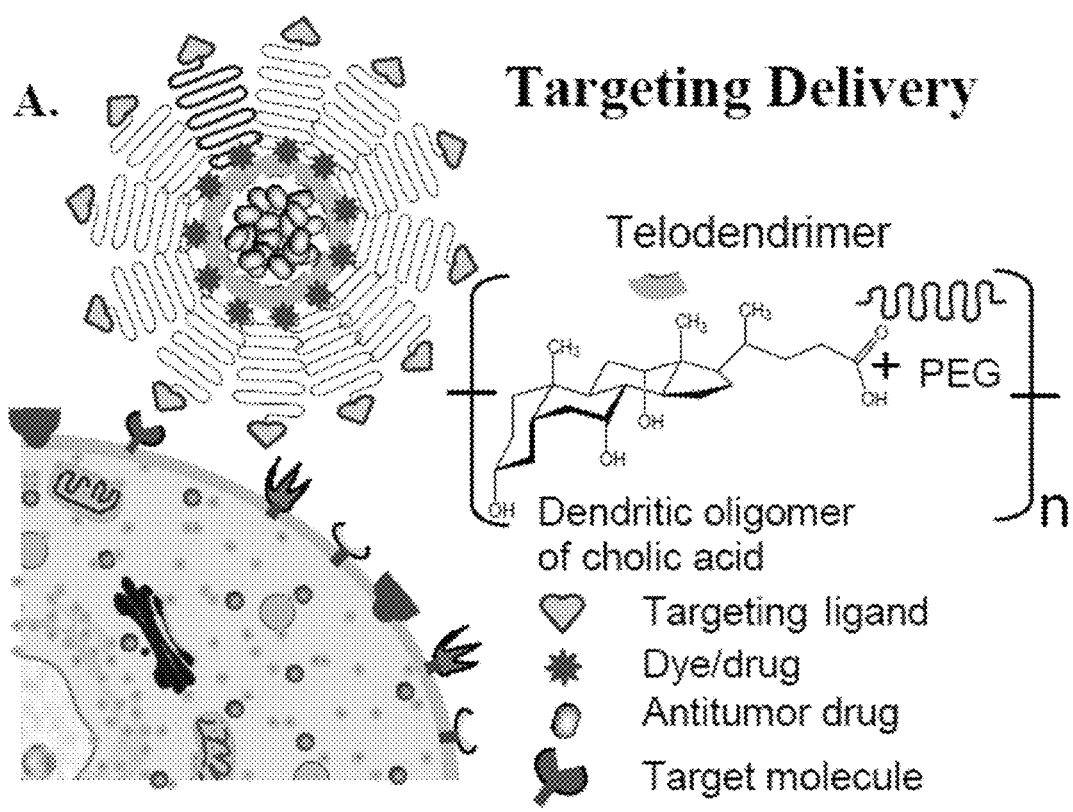
FIGS. 2A-C illustrate characterization of targeting nanomicelles. A. Schematic diagram. B. Size determination of nanomicelles with dynamic light scattering (DLS). The median size of nanomicelles loaded with daunorubicin, and coated with CLL1-targeting peptide was about 13.5 nm with narrow size distribution. C. Transmission electron microscopy of targeting nanomicelles. The bar length represents 50 nm.
Figure 2B:
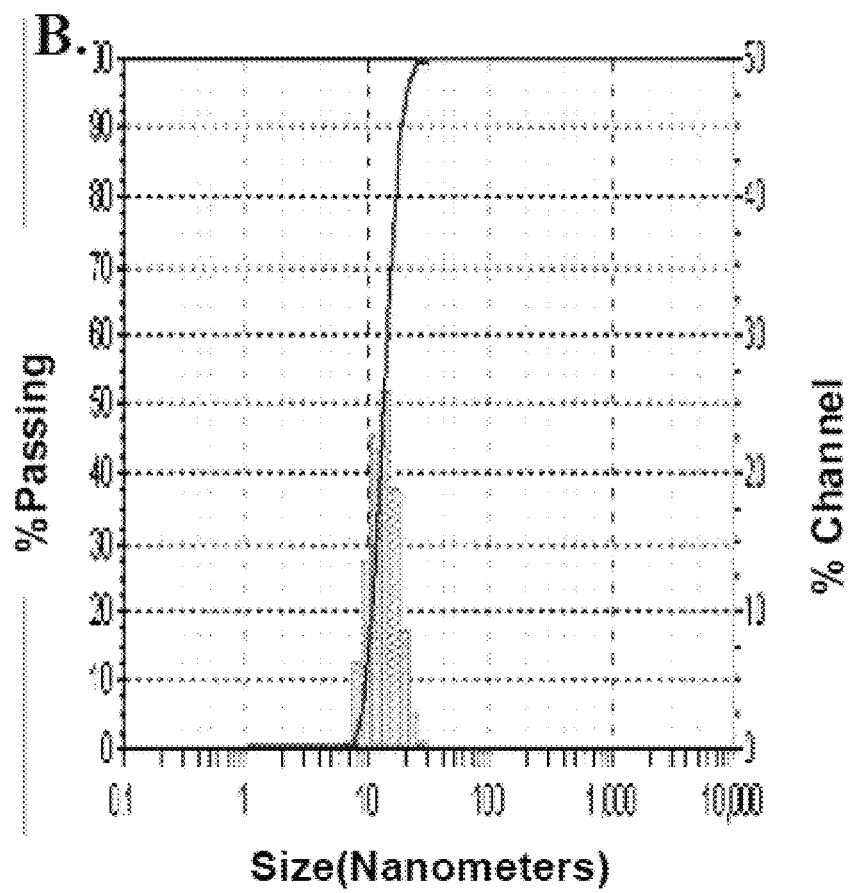
Figure 2C:
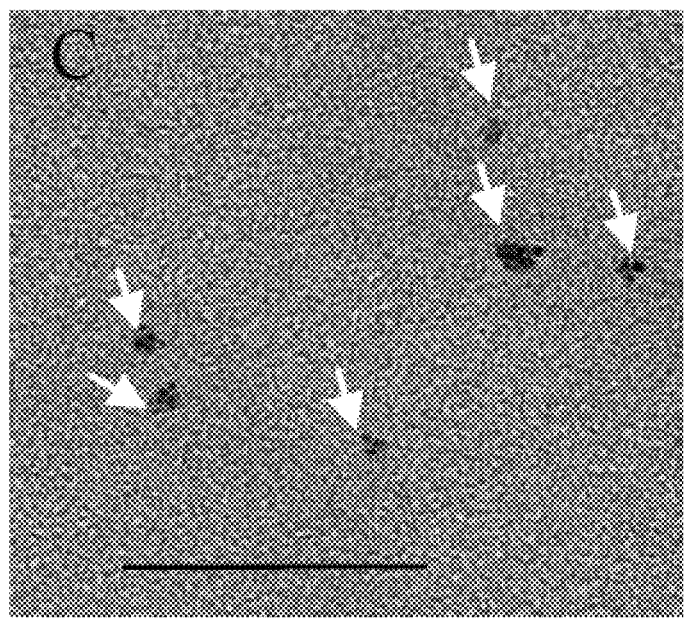

It was determined whether CLL-L1 could be used to develop targeting nanotherapeutics by displaying CLL-L1 on the surface of our recently developed nanomicelles (FIG. 2A). The average size of the targeting nanomicelle was approximately 13.5 nm with a narrow size distribution (FIG. 2B). This size distribution was confirmed with transmission electron microscopy (FIG. 2C). The size of the nanomicelles is attractive for treating LSC since the particles are small enough to easily distribute though the vasculature and bone marrow, but are large enough to retard the nanomicelles in blood circulation. DNR is one of the only two first-line chemotherapeutic drugs (together with cytarabine) for AML. The drug loading capacity was determined, and found that up to 5 mg of DNR could be loaded in 20 mg of telodendrimer. Considering a typical clinical dose of DNR is 45 mg/m$^2$, this is equivalent to a telodendrimer dose (the nanomicelle monomer units) of 225 mg/m$^2$. This dose of telodendrimer is well below the non-toxic level of telodendrimer at 1 mg/ml in cell culture [Xiao, et al., Biomaterials (2009) 30:6006-6016], and less than one fourth of the telodendrimer dose used in dog studies when the nanomicelles were loaded with paclitaxel, another chemotherapeutic drug. This suggests that the dose of telodendrimer of our targeting nanomicelle is within the tolerable range and that toxicity will be limited by the total dose of DNR. Further preclinical and clinical trials will be performed to determine the toxicity of DNR in the nanomicelle formulation.

Cellular Uptake of CLL1-Targetting Nanomicelles

Figure 3A:
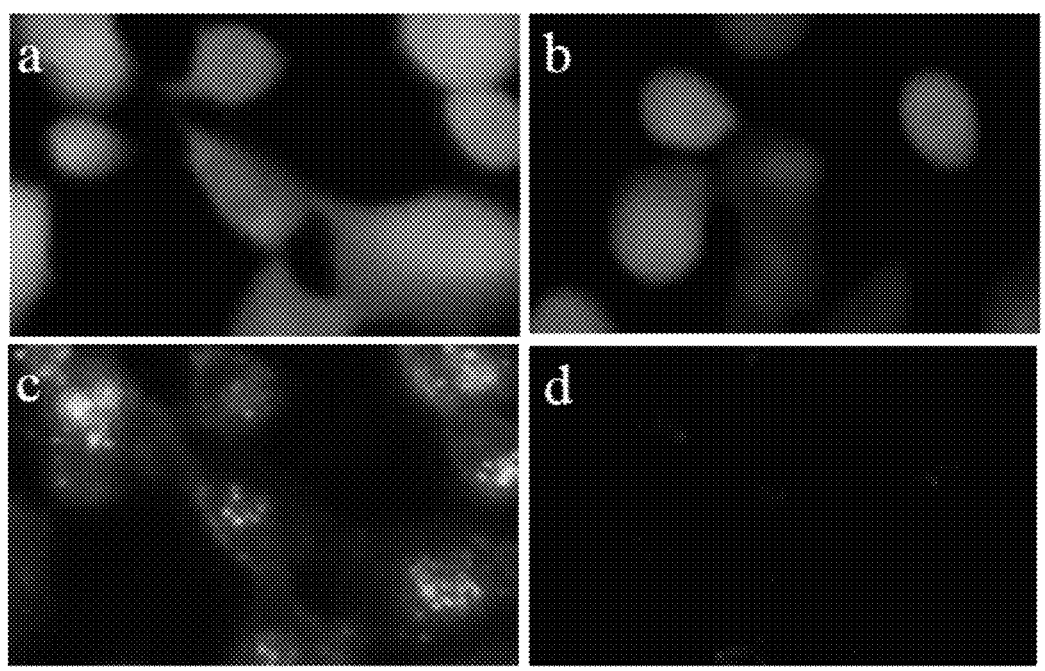
FIGS. 3A-C illustrate penetration of targeting nanomicelles to A549 cells expressing CLL1. A. preferential uptake of targeting nanomicelles by A549 cells expressing CLL1. Targeting nanomicelles were loaded with DiI and coated with CLL1-targeting peptides. A549 cells expressing GFP-CLL1 (panel a) or GFP (panel b, control) were incubated with nanomicelles for 30 minutes. Strong fluorescence was observed in A549 cells expressing GFP-CLL1 (panel c), but not in A549 cells expressing GFP (panel d). B. Tomography analysis to determine intracellular distribution of targeting nanomicelles. A549 cells expressing GFP-CLL1 (panel a) or GFP (panel b) were incubated with targeting nanomicelles loaded with DiI for 15 minutes before washing. C. Preferential delivery of targeting nanomicelles to A549 cells expressing CLL1. A549 cells expressing CLL1 were incubated with non-targeting or targeting nanomicelles loaded with DiI (upper panel) or DNR (lower panel) for 30 minutes before washing. Because of non-specific uptake of nanomicelles by cells, there was no plateau of fluorescence intensity as the concentration of nanomicelle increased. *p<0.05. **p<0.001.

It was determined whether CLL1-L1 could enable the drug-loaded nanomicelles to be taken up into cells expressing CLL1 and deliver the cytotoxic cargo across the cell membrane. This is important in order for targeting nanomicelles to overcome the relatively high drug resistance of LSC. Since visualizing the binding and drug delivery of nanomicelles to LSC is technically demanding in suspension cells with little cytoplasm, we chose to work with adherent A549 cells transfected with GFP-CLL1 as a model system (FIG. 3A Panel a). A549 cells transfected with GFP vector alone were used as the negative control (FIG. 3A panel b). Nanomicelles were loaded with DiI, which exhibits intense red fluorescence, as a model for DNR for monitoring delivery and intracellular distribution. Within ten minutes of incubation, strong DiI fluorescence was visible in A549 cells that expressed GFP-CLL1 (FIG. 3A panel c), but not in control A549 cells expressing GFP (FIG. 3A panel d). However, these experiments lacked sufficient resolution to differentiate whether the DiI was on the surface or inside the cells.

Figure 3B:
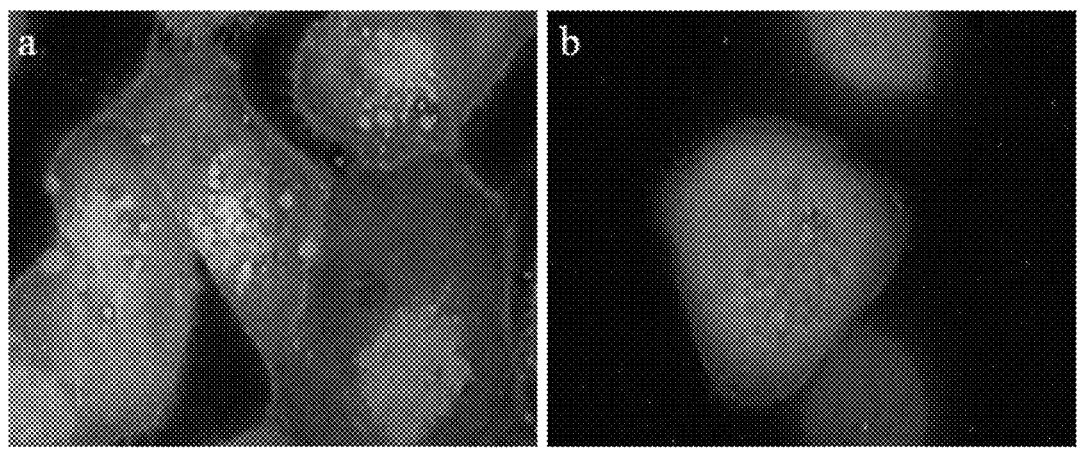
Figure 3C:
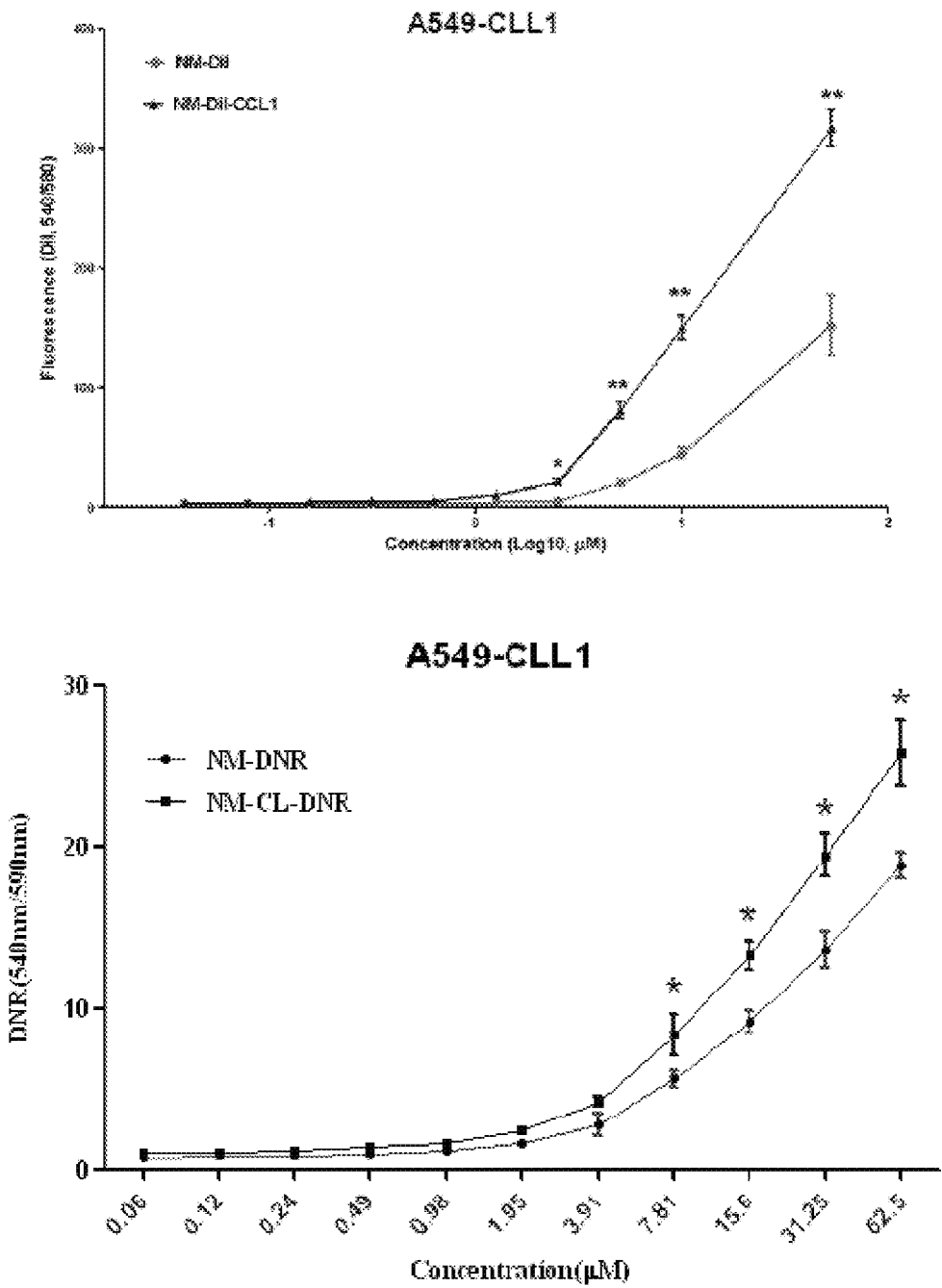

To determine if the DiI-loaded targeting nanomicelles could penetrate into cells, high resolution 3-dimensional microscopy was performed with the DeltaVision system. The images were then deconvolved using a known optical transfer function and DeltaVision software algorithms per manufacturer's protocol. To mimic the in vivo metabolism and clearance of nanomicelles, cells were incubated with the DiI-loaded targeting nanomicelles for 15 minutes and washed with PBS to remove any unbound nanomicelles. Red fluorescence (nanomicelle loaded with DiI) was not only localized on the cell membrane, but, strikingly, the DiI was transported to the cell interior, including nucleus, of the cells expressing GFP-CLL1 (FIG. 3B panel a), while no significant red fluorescence was observed in the control cells transfected with GFP vector only (FIG. 3B panel b). To quantify the drug delivery, the same number of A549 cells, expressing GFP or CLL1-GFP, were treated with the identical concentrations of DiI- or DNR-loaded nanomicelles. There was a dose-dependent and statistically significant difference in drug delivery between the targeting and non-targeting nanomicelles (FIG. 3C, upper panel: nanomicelles loaded with DiI, lower panel: nanomicelles loaded with DNR). These data suggest that drugs loaded into targeting nanomicelles can be delivered preferentially into cells that express CLL1.

Targeting Nanomicelles Coated with CLL1-L1 Targets LSC from Clinical Specimens

Figure 4A:
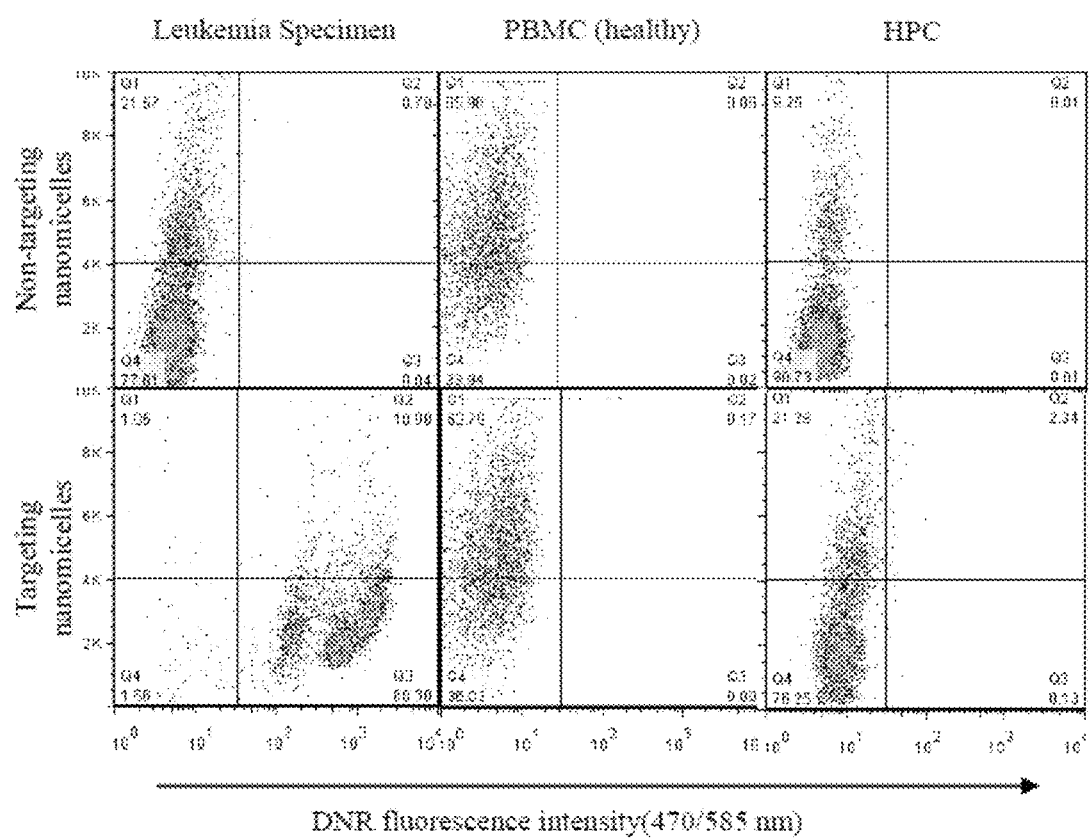
FIGS. 4A-C illustrate targeting leukemic cells with nanomicelles decorated with CLL1-targeting peptides. A. comparison of targeting between PMBC, normal hematopoietic stem cells (NHSC), and leukemia cells. Cells were incubated with non-targeting (upper panels) or targeting (lower panels) nanomicelles loaded with DNR for 30 minutes, and analyzed with flow cytometry after washing. X-axis: DNR fluorescence intensity. Y-axis: side gate for cell size. B. Drug delivery against CD34(+) clinical leukemic cells. CD34(+) clinical leukemic cells were incubated with targeting (left panels) or non-targeting (right panels) nanomicelles, both loaded with DNR, at different concentration for 30 minutes before flow cytometry analysis. C. Dose-dependent targeting against CD34(+) clinical leukemic cells. CD34(+) clinical leukemic cells were incubated with targeting (left panels) or nontargeting (right panels) nanomicelles, both loaded with DiI, at different concentration for 30 minutes before flow cytometry analysis. Control: cells were treated with nanomicelles not loaded with DiI. The concentrations shown at the left of each row were DiI concentration.
Figure 4B:
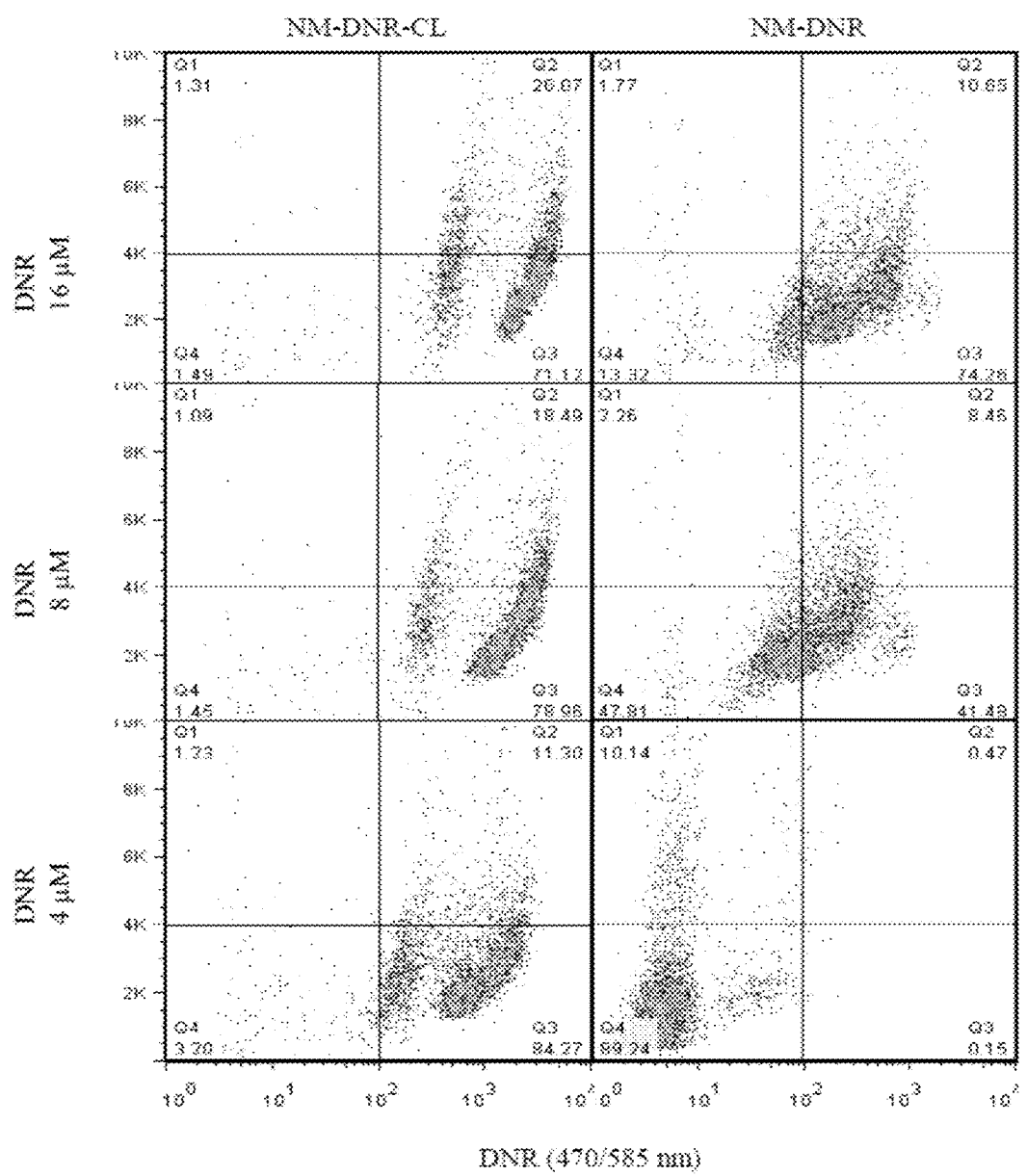
Figure 4C:
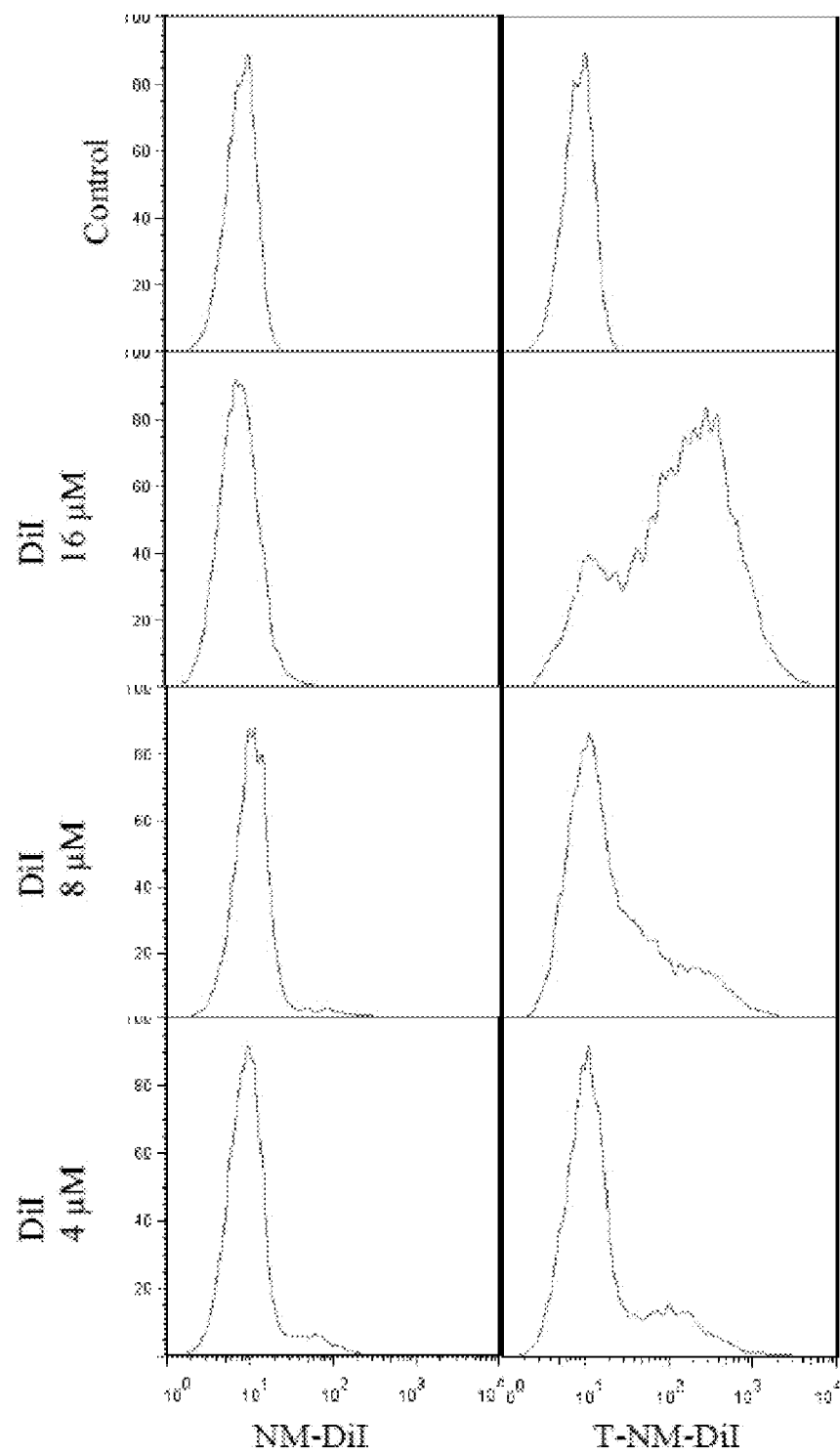
Figure 5:
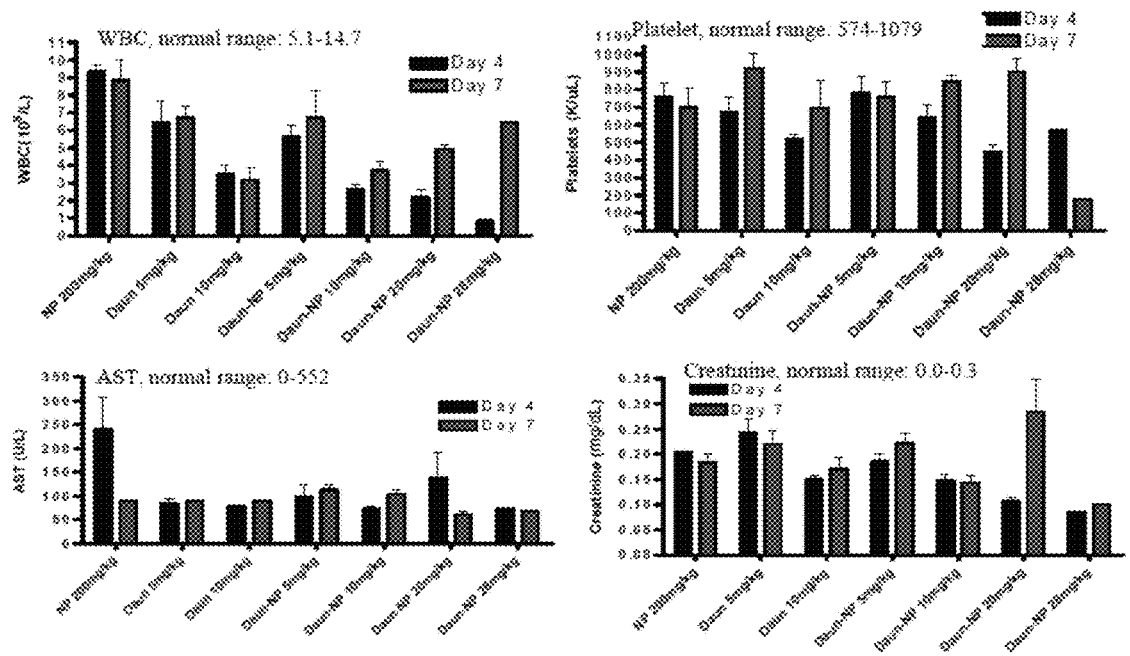
FIG. 5 illustrates toxicology studies in Balb/c mice comparing empty nanomicelle at 200 mg/kg, free DNR at 5 and 10 mg/kg, DNR in nanomicelle at 5, 10, 20 and 28 mg/kg (From left to right of each panel). The therapeutic dose and maximum tolerated dose of free parental DNR are 5 and 10 mg/kg of body weight in Balb/c mice, respectively. In the Balb/c mice that received empty nanomicelles, free DNR or DNR in nanomicelles, no significant weight changes were seen during the follow-up for up to 10 days. The complete blood count (CBC) and chemistry panel (AST, ALT, total bilirubin, BUN and creatinine levels) in mice that received DNR in the nanomicelle formulation up to 20 mg/kg were not statistically significantly different from the mice that received free DNR at 5 mg/kg. Excepting leukopenia (Panel A), no significant changes of blood count or serum chemistry were observed in mice treated with DNR in nanomicelle up to 20 mg/kg, 4 times the therapeutic dose. The dose at 28 mg/kg seemed to be too toxic as profound leukopenia (Panel A) thrombocytopenia (Panel B) and increase in BUN were observed.
Figure 6:
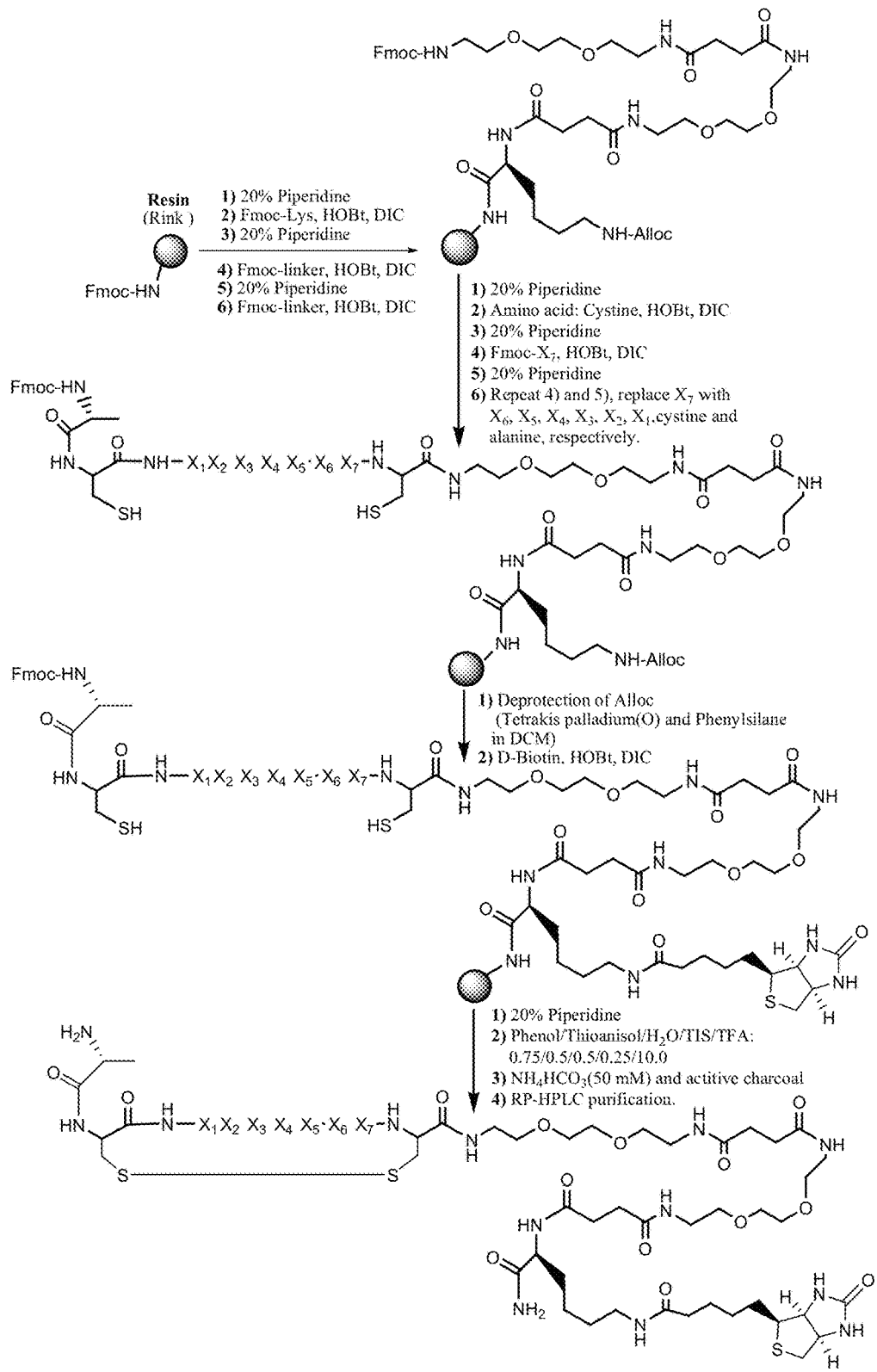
FIG. 6 illustrates synthesis of biotinylated peptide.
Figure 7:
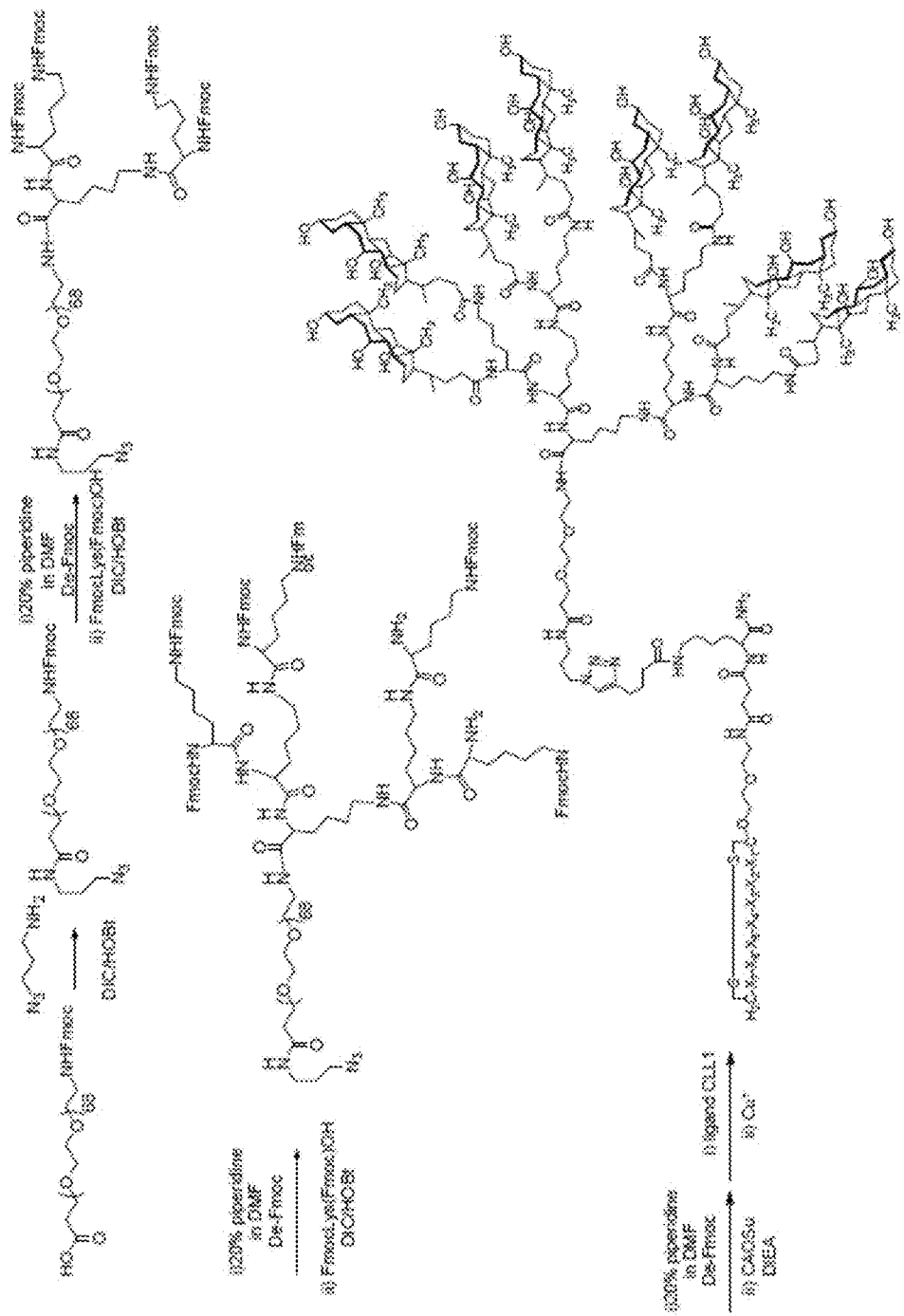
FIG. 7 illustrates synthesis of nanoparticle of CLL1 ligand.

It was determined whether targeting nanomicelles decorated with CLL1-L1 could target clinical leukemia specimens from AML patients. First, the drug delivery between leukemic cells, PBMC and normal hematopoietic stem cells was compared. These cells were incubated with non-targeting or targeting nanomicelles, both loaded with DNR. Substantial DNR delivery was observed for leukemic cells exposed to targeting nanomicelles, while little delivery was observed with PBMC and normal hematopoietic stem cells (FIG. 4A). The existence of a dose-dependent drug delivery difference was investigated between nontargeting and targeting nanomicelles to CD34+ leukemic cells (FIGS. 4 B and C). After incubation CD34+ cells with non-targeting or targeting nanomicelles at different concentration for 30 minutes, cells were washed with PBS and analyzed with flow cytometry. There was a dose-dependent difference in drug delivery between these two types of nanomicelles (FIG. 4, B: nanomicelles loaded with DNR; C: nanomicelles loaded with DiI). So far, we tested four leukemia specimens. The targeting nanomicelles could target three out of the four specimens, which is consistent with a previous report that not all LSCs express CLL1 [Bakker, et al., *Cancer Res* (2004) 64:8443-8450].

Discussion

This is the first report demonstrating the screening and synthesis of peptides that specifically bind to cells expressing CLL1 and with low nonspecific binding to other cell types. The CLL1 molecule is expressed on LSC, but not on normal hematopoietic stem cells, which makes it an attractive cell surface target for LSC-seeking nanotherapeutics. It was also shown that nanomicelles decorated with CLL1-targeting peptides bind to cells expressing CLL1, but more importantly, can deliver the drug load directly into the target cells.

The targeting nanomicelles developed in this project can potentially improve the treatment outcomes of AML through the following three mechanisms: (1) targeting LSC through direct drug delivery into the interior of LSC; (2) killing of leukemia cells throughout the body with chemotherapeutic drugs released from nanomicelles into blood circulation; and (3) formulation of chemotherapeutic drugs inside the nanoparticles allowing administration of high-dose chemotherapy without increasing the toxicity.

One major concern in targeting LSC is whether the targeting nanomicelles can deliver sufficient drug concentration to LSC to overcome the chemoresistance and improve the treatment outcomes of AML. Based on our calculations and available data described below, drug concentration delivered by targeting nanomicelles are sufficient to overcome the resistance at least in some patients. It has been shown that high-dose chemotherapy itself can improve treatment outcomes and prolong overall survival as demonstrated in the Eastern Cooperative Oncology Group (ECOG) 1900 trial (DNR at 90 mg/m$^2$ versus the standard dose of 45 mg/m$^2$) [Information NaPR: High Dose Chemotherapy Significantly Prolongs Survival for Patients with Acute Myeloid Leukemia. In, Cancer News on the Net®, (2008); Fernandez, *N Engl J Med* (2009) 361:1249-1259; and Lowenberg, et al., *N Engl J Med* (2009) 361:1235-1248]. Higher doses (135 mg/m$^2$) of DNR in the liposomal formulation together with cytarabine could be delivered and induce complete remission in refractory or recurrent AML [Cortes, et al., *Cancer* (2001) 92:7-14]. It has also been shown that paclitaxel, another chemotherapeutic drug, could be loaded in our nanomicelle and administered at three times the maximum tolerated dose of the free parental drug, which significantly improved the treatment outcomes in mice without increasing the toxicity [Xiao, et al., *Biomaterials* (2009) 30:6006-6016]. Decoration on the surface of paclitaxel-loaded nanomicelles with β-integrin targeting peptides could induce long-term remission by enhancing penetration of the drug into tumor tissues. Compared to the therapeutic dose of DNR in mice at 5 mg/kg of body weight, two to four times the therapeutic dose (10-20 mg/kg) of DNR in nanomicelles could be given without any significant changes of body weight, CBC and serum chemistry panel. This suggests that the nanomicelle itself can potentially improve treatment outcomes for AML just by re-formulating DNR in nanomicelles. The nanomicelles are covered with PEG rendering them "stealthy" with low non-specific uptake. This decreased toxicity itself will improve treatment outcomes since the 4-week mortality rate during the induction chemotherapy ranges from 5% to 57% [Estey, *Cancer* (2001) 92:1059-1073].

The data provided herein support the feasibility of using targeting nanomicelles to deliver DNR or other drugs into LSC as a means to overcome resistance mediated by cancer stem cells. When nanomicelles were decorated with CLL1-L1, consistently high concentrations of DNR were observed in cells expressing CLL1-L1 and in clinical leukemia specimens (FIGS. 3 and 4). Furthermore, the drug load was observed at the nucleus (FIG. 3B), suggesting the targeting nanomicelles were able to deliver the alkylating agent DNR proximally to its DNA target. In addition, the nanomicelle platform can allow us to simultaneously load different drugs into the same nanomicelles. For example, DNR can be co-loaded with drugs targeting apoptosis, or combined with small interfering RNA (siRNA) to target anti-apoptosis or other drug-resistant mechanisms, making them more efficacious. However, the in vivo anti-leukemia efficacy and toxicity of DNR-loaded targeting nanomicelle need to be determined by clinical trials.

LSC are a common phenomenon in AML except in the promyelocytic leukemia. Targeting LSC surface molecules has been reported to decrease the engraftment of AML in animal models [Feuring-Buske, et al, *Cancer Res* (2002) 62:1730-1736; Hogge, et al., *Clin Cancer Res* (2006) 12:1284-1291; Jin, et al., *Cell Stem Cell* (2009) 5:31-42], suggesting that eradication of LSC is an important step in treating AML. However, targeting and killing LSC alone may not be sufficient in the eradication of AML. LSC account for a small population of all leukemia cells. Even if all LSC are eliminated, the remaining leukemia cells and their progenitor cells can continue to cause symptoms. Furthermore, the progenitor cells may still have limited proliferation capacity and generate more leukemia cells, or may even de-differentiate back into LSC. This is supported by a clinical trial demonstrating that the anti-CD20 antibody rituximab as a single agent is not effective in multiple myeloma, even though myeloma stem cells express the CD20 cell surface molecules [Zojer, et al., *Leuk Lymphoma* (2006) 47:1103-1109; Matsui, et al., *Blood* (2004) 103:2332-2336]. The advantage of our targeting nanomicelles is that not only are LSC targeted, but the loaded drugs can be potentially released into systemic circulation and kill leukemia cells throughout the body.

So far, no molecule has been identified that is specific to cancer stem cells. CLL1 and CD123 are two molecules expressed on LSC, but not on normal hematopoietic stem cells. Anti-CD123 therapy, either with neutralizing antibodies or immunotoxins, preferentially kills AML LSC with little effect on normal stem cells, and decreases the effectiveness of AML engraftment in NOD-SCID mice [Feuring-Buske, et al, *Cancer Res* (2002) 62:1730-1736; Hogge, et al., *Clin Cancer Res* (2006) 12:1284-1291; Jin, et al., *Cell Stem Cell* (2009) 5:31-42]. Similar anti-leukemia activity was also recently observed with an anti-CLL1 antibody [Zhao, et al., *Haematologica* (2010) 95:71-78]. However, these two molecules are also expressed on some normal hematopoietic cells. If antibody is used to target these two molecules, the long half-life of antibody (weeks to months) will kill the newly regenerated hematopoietic cells and may affect the hematological recovery because both CD123 and CLL1 are also expressed on normal hematopoietic cells. The advantage of our targeting nanomicelles over antibody-based therapy is its short in vivo half-life of less than 24 hours. The targeting nanomicelles described herein are expected to kill some normal hematopoietic cells as any other chemotherapeutic agents do, but the short half-life means that the subsequently newly regenerated hematopoietic cells will not be affected.

In conclusion, several peptides have been identified that target CLL1, a molecule that is expressed on LSC surface, but not on normal hematopoietic stem cells. Nanomicelles decorated with CLL1-targeting peptides allow delivery of the drug load directly into and eradicate LSC.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

---

What is claimed is:

1. A method of detecting the presence of a leukemia stem cell (LSC) expressing C-type lectin-like molecule-1 (CLL1), comprising contacting the LSC with a peptide comprising the amino acid sequence motif LR(S/T), wherein the peptide is no longer than 10 amino acids in length and binds to C-type lectin-like molecule-1 (CLL1), wherein the peptide is linked to a detectable label, and detecting the binding of the peptide to the LSC.

2. The method of claim 1, wherein the detectable label is selected from the group consisting of a bead, a fluorophore, a chemiluminescent moiety, a nanoparticle, a magnetic particle, a metal particle or a radioisotope.

3. The method of claim 1, wherein the LSC is in vitro.

4. The method of claim 1, wherein the LSC is in vivo.

5. The method of claim 1, wherein the LSC are in a population of blood cells.

6. A method of inhibiting, reducing or preventing the growth or proliferation of a leukemia stem cell (LSC) expressing C-type lectin-like molecule-1 (CLL1) in a subject in need thereof, comprising contacting the LSC with a peptide comprising the amino acid sequence motif LR(S/T), wherein the peptide is no longer than 10 amino acids in length and binds to C-type lectin-like molecule-1 (CLL1), wherein the peptide binds to LSC and the therapeutic moiety inhibits or prevents the growth or proliferation of the LSC.

7. The method of claim 6, wherein the therapeutic moiety is an Fc portion of an immunoglobulin, a cytotoxin, a nanoparticle, a liposome or a chemotherapeutic agent.

8. The method of claim 6, wherein the therapeutic moiety is a chemotherapeutic agent encapsulated in a nanoparticle.

9. The method of claim 6, wherein the subject is a human.

10. The method of claim 6, wherein the peptide linked to the therapeutic moiety is administered to the subject intravenously or into the bone marrow.

11. The method of claim 6, wherein the peptide comprises the amino acid sequence $X_1LRX_4X_5X_6X_7$ (SEQ ID NO: 1), wherein:

$X_1$ is any amino acid;
$X_4$ is S or T;
$X_5$ is A, S or F;
$X_6$ is A, G or S; and
$X_7$ is A, V, P or F.

12. The method of claim 6, wherein the peptide comprises the amino acid sequence $X_1LRX_4X_5X_6X_7$ (SEQ ID NO: 2), wherein:

$X_1$ is any amino acid;
$X_4$ is S or T;
$X_5$ is A or S;
$X_6$ is A or G; and
$X_7$ is A, V or P.

13. The method of claim 6, wherein the peptide comprises the amino acid sequence $X_1LRX_4AAX_7$ (SEQ ID NO: 4), wherein:

$X_1$ is any amino acid;
$X_4$ is S or T; and
$X_7$ is A or V.

14. The method of claim 6, wherein the peptide comprises the amino acid sequence $X_1LRX_4AAV$ (SEQ ID NO: 3), wherein:

$X_1$ is any amino acid; and
$X_4$ S S or T.

15. The method of claim 11, wherein $X_1$ is P, D, L, T or A.

16. The method of claim 6, wherein the peptide comprises the amino acid sequence $X_1LRSSGP$ (SEQ ID NO: 5), wherein $X_1$ is any amino acid.

17. The method of claim 11, wherein $X_1$ is V, S, P or T.

18. The method of claim 6, wherein the peptide is selected from the group consisting of PLRSAAA (SEQ ID NO: 6), DLRSAAV (SEQ ID NO: 7), LLRTAAV (SEQ ID NO: 8), LLRSAAV (SEQ ID NO: 9), TLRTAAV (SEQ ID NO: 10), ALRSAAV (SEQ ID NO: 11), VLRSSGP (SEQ ID NO: 12), SLRSSGP (SEQ ID NO: 13), PLRSSGP (SEQ ID NO: 14), TLRSSGP (SEQ ID NO: 15), and PTPPFSF (SEQ ID NO: 16).

19. The method of claim 6, wherein:
  i) one or more of the amino acid residues are D-amino acids;
  ii) the peptide comprises protecting groups at one or both of the N-terminus or the C terminus;
  iii) the peptide is fully or partially retro-inverso;
  iv) the peptide comprises 2 or more repeats; or
  v) the peptide is circularized.

20. The method of claim 6, wherein the peptide is DLRSAAV (SEQ ID NO:7).

21. The method of claim 6, wherein the peptide is CDLRSAAVC (SEQ ID NO:17).

22. The method of claim 1, wherein the peptide comprises the amino acid sequence $X_1LRX_4X_5X_6X_7$ (SEQ ID NO: 1), wherein:
  $X_1$ is any amino acid;
  $X_4$ is S or T;
  $X_5$ is A, S or F;
  $X_6$ is A, G or S; and
  $X_7$ is A, V, P or F.

23. The method of claim 1, wherein the peptide comprises the amino acid sequence $X_1LRX_4X_5X_6X_7$ (SEQ ID NO: 2), wherein:
  $X_1$ is any amino acid;
  $X_4$ is S or T;
  $X_5$ is A or S;
  $X_6$ is A or G; and
  $X_7$ is A, V or P.

24. The method of claim 1, wherein the peptide comprises the amino acid sequence $X_1LRX_4AAX_7$ (SEQ ID NO: 4), wherein:
  $X_1$ is any amino acid;
  $X_4$ is S or T; and
  $X_7$ is A or V.

25. The method of claim 1, wherein the peptide comprises the amino acid sequence $X_1LRX_4AAV$ (SEQ ID NO: 3), wherein:
  $X_1$ is any amino acid; and
  $X_4$ is S or T.

26. The method of claim 22, wherein $X_1$ is P, D, L, T or A.

27. The method of claim 1, wherein the peptide comprises the amino acid sequence $X_1LRSSGP$ (SEQ ID NO: 5), wherein $X_1$ is any amino acid.

28. The method of claim 22, wherein $X_1$ is V, S, P or T.

29. The method of claim 1, wherein the peptide is selected from the group consisting of PLRSAAA (SEQ ID NO: 6), DLRSAAV (SEQ ID NO: 7), LLRTAAV (SEQ ID NO: 8), LLRSAAV (SEQ ID NO: 9), TLRTAAV (SEQ ID NO: 10), ALRSAAV (SEQ ID NO: 11), VLRSSGP (SEQ ID NO: 12), SLRSSGP (SEQ ID NO: 13), PLRSSGP (SEQ ID NO: 14), TLRSSGP (SEQ ID NO: 15), and PTPPFSF (SEQ ID NO: 16).

30. The method of claim 1, wherein the peptide is DLRSAAV (SEQ ID NO:7).

31. The method of claim 1, wherein the peptide is CDLRSAAVC (SEQ ID NO:17).

32. The method of claim 1, wherein:
  i) one or more of the amino acid residues are D-amino acids;
  ii) the peptide comprises protecting groups at one or both of the N-terminus or the C terminus;
  iii) the peptide is fully or partially retro-inverso;
  iv) the peptide comprises 2 or more repeats; or
  v) the peptide is circularized.

* * * * *

SEQUENCE LISTING

```
<160> NUMBER OF SEQ ID NOS: 34

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (4)..(4)
<223> OTHER INFORMATION: Ser or Thr
<220> FEATURE:
<221> NAME/KEY: MOD_RES
<222> LOCATION: (5)..(5)
<223> OTHER INFORMATION: Ala, Ser or Phe
<220> FEATURE:
<221> NAME/KEY: MOD_RES
<222> LOCATION: (6)..(6)
<223> OTHER INFORMATION: Ala, Gly or Ser
<220> FEATURE:
<221> NAME/KEY: MOD_RES
<222> LOCATION: (7)..(7)
<223> OTHER INFORMATION: Ala, Val, Pro or Phe

<400> SEQUENCE: 1

Xaa Leu Arg Xaa Xaa Xaa Xaa
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (4)..(4)
<223> OTHER INFORMATION: Ser or Thr
<220> FEATURE:
```

```
<221> NAME/KEY: MOD_RES
<222> LOCATION: (5)..(5)
<223> OTHER INFORMATION: Ala or Ser
<220> FEATURE:
<221> NAME/KEY: MOD_RES
<222> LOCATION: (6)..(6)
<223> OTHER INFORMATION: Ala or Gly
<220> FEATURE:
<221> NAME/KEY: MOD_RES
<222> LOCATION: (7)..(7)
<223> OTHER INFORMATION: Ala, Val or Pro

<400> SEQUENCE: 2

Xaa Leu Arg Xaa Xaa Xaa Xaa
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (4)..(4)
<223> OTHER INFORMATION: Ser or Thr
<220> FEATURE:
<223> OTHER INFORMATION: see specification as filed for detailed
      description of substitutions and preferred embodiments

<400> SEQUENCE: 3

Xaa Leu Arg Xaa Ala Ala Val
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (4)..(4)
<223> OTHER INFORMATION: Ser or Thr
<220> FEATURE:
<221> NAME/KEY: MOD_RES
<222> LOCATION: (7)..(7)
<223> OTHER INFORMATION: Ala or Val
<220> FEATURE:
<223> OTHER INFORMATION: see specification as filed for detailed
      description of substitutions and preferred embodiments

<400> SEQUENCE: 4

Xaa Leu Arg Xaa Ala Ala Xaa
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: Any amino acid
<220> FEATURE:
<223> OTHER INFORMATION: see specification as filed for detailed
      description of substitutions and preferred embodiments

<400> SEQUENCE: 5

Xaa Leu Arg Ser Ser Gly Pro
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Pro Leu Arg Ser Ala Ala Ala
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Leu Arg Ser Ala Ala Val
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Leu Arg Thr Ala Ala Val
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Leu Arg Ser Ala Ala Val
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10
```

```
Thr Leu Arg Thr Ala Ala Val
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Leu Arg Ser Ala Ala Val
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Val Leu Arg Ser Ser Gly Pro
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Leu Arg Ser Ser Gly Pro
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Pro Leu Arg Ser Ser Gly Pro
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Thr Leu Arg Ser Ser Gly Pro
1               5

<210> SEQ ID NO 16
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 16

Pro Thr Pro Pro Phe Ser Phe
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Cys Asp Leu Arg Ser Ala Ala Val Cys
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid other than Cys
<220> FEATURE:
<221> NAME/KEY: MOD_RES
<222> LOCATION: (5)..(5)
<223> OTHER INFORMATION: Ser or Thr
<220> FEATURE:
<221> NAME/KEY: MOD_RES
<222> LOCATION: (6)..(6)
<223> OTHER INFORMATION: Ala, Ser or Phe
<220> FEATURE:
<221> NAME/KEY: MOD_RES
<222> LOCATION: (7)..(7)
<223> OTHER INFORMATION: Ala, Gly or Ser
<220> FEATURE:
<221> NAME/KEY: MOD_RES
<222> LOCATION: (8)..(8)
<223> OTHER INFORMATION: Ala, Val, Pro or Phe
<220> FEATURE:
<223> OTHER INFORMATION: see specification as filed for detailed
      description of substitutions and preferred embodiments

<400> SEQUENCE: 18

Cys Xaa Leu Arg Xaa Xaa Xaa Xaa Cys
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid other than Cys
<220> FEATURE:
<221> NAME/KEY: MOD_RES
<222> LOCATION: (5)..(5)
<223> OTHER INFORMATION: Ser or Thr
<220> FEATURE:
<221> NAME/KEY: MOD_RES
<222> LOCATION: (6)..(6)
```

<223> OTHER INFORMATION: Ala or Ser
<220> FEATURE:
<221> NAME/KEY: MOD_RES
<222> LOCATION: (7)..(7)
<223> OTHER INFORMATION: Ala or Gly
<220> FEATURE:
<221> NAME/KEY: MOD_RES
<222> LOCATION: (8)..(8)
<223> OTHER INFORMATION: Ala, Val or Pro
<220> FEATURE:
<223> OTHER INFORMATION: see specification as filed for detailed
      description of substitutions and preferred embodiments

<400> SEQUENCE: 19

Cys Xaa Leu Arg Xaa Xaa Xaa Xaa Cys
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid other than Cys
<220> FEATURE:
<221> NAME/KEY: MOD_RES
<222> LOCATION: (4)..(4)
<223> OTHER INFORMATION: Ser or Thr
<220> FEATURE:
<221> NAME/KEY: MOD_RES
<222> LOCATION: (7)..(7)
<223> OTHER INFORMATION: Ala or Val
<220> FEATURE:
<223> OTHER INFORMATION: see specification as filed for detailed
      description of substitutions and preferred embodiments

<400> SEQUENCE: 20

Xaa Leu Arg Xaa Ala Ala Xaa
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid other than Cys
<220> FEATURE:
<221> NAME/KEY: MOD_RES
<222> LOCATION: (5)..(5)
<223> OTHER INFORMATION: Ser or Thr
<220> FEATURE:
<223> OTHER INFORMATION: see specification as filed for detailed
      description of substitutions and preferred embodiments

<400> SEQUENCE: 21

Cys Xaa Leu Arg Xaa Ala Ala Val Cys
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic

```
            peptide
<220> FEATURE:
<221> NAME/KEY: MOD_RES
<222> LOCATION: (2)..(2)
<223> OTHER INFORMATION: Any amino acid other than Cys
<220> FEATURE:
<223> OTHER INFORMATION: see specification as filed for detailed
      description of substitutions and preferred embodiments

<400> SEQUENCE: 22

Cys Xaa Leu Arg Ser Ser Gly Pro Cys
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Cys Pro Leu Arg Ser Ala Ala Ala Cys
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid

<400> SEQUENCE: 24

Cys Xaa Leu Arg Ser Ser Gly Pro Cys
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Cys Leu Leu Arg Thr Ala Ala Val Cys
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Cys Leu Leu Arg Ser Ala Ala Val Cys
1               5

<210> SEQ ID NO 27
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 27

Cys Thr Leu Arg Thr Ala Ala Val Cys
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Cys Ala Leu Arg Ser Ala Ala Val Cys
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Cys Val Leu Arg Ser Ser Gly Pro Cys
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Cys Ser Leu Arg Ser Ser Gly Pro Cys
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Cys Pro Leu Arg Ser Ser Gly Pro Cys
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Cys Thr Leu Arg Ser Ser Gly Pro Cys
1               5
```

```
<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Cys Pro Thr Pro Pro Phe Ser Phe Cys
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(5)
<223> OTHER INFORMATION: Ser or Thr

<400> SEQUENCE: 34

Cys Xaa Leu Arg Xaa Ala Ala Val Cys
1               5
```